(12) United States Patent
Harder et al.

(10) Patent No.: US 10,795,879 B2
(45) Date of Patent: Oct. 6, 2020

(54) METHODS AND SYSTEMS FOR PREDICTIVE CLINICAL PLANNING AND DESIGN

(71) Applicant: IQVIA INC., Parsippany, NJ (US)

(72) Inventors: Donald R. Harder, Fishers, IN (US); Daniel D. Siders, Westfield, IN (US); Leslie Thomas, Indianapolis, IN (US); Sara L. Zembrodt, Indianapolis, IN (US)

(73) Assignee: IQVIA Inc., Parsippany, NJ (US)

( * ) Notice: Subject to any disclaimer, the term of this patent is extended or adjusted under 35 U.S.C. 154(b) by 567 days.

(21) Appl. No.: 15/427,205

(22) Filed: Feb. 8, 2017

(65) Prior Publication Data

US 2017/0147794 A1    May 25, 2017

Related U.S. Application Data

(63) Continuation-in-part of application No. 14/947,726, filed on Nov. 20, 2015, now Pat. No. 9,600,637, (Continued)

(51) Int. Cl.
*G06F 17/30* (2006.01)
*G06F 16/23* (2019.01)
(Continued)

(52) U.S. Cl.
CPC ........ *G06F 16/2365* (2019.01); *G06F 16/248* (2019.01); *G06F 17/10* (2013.01); *G06F 40/14* (2020.01); *G06F 40/166* (2020.01); *G06T 11/206* (2013.01); *G16H 10/20* (2018.01); *G16H 10/60* (2018.01); *G16H 40/63* (2018.01); *G06T 2200/24* (2013.01)

(58) Field of Classification Search
CPC .... G06F 16/2365; G06F 16/248; G06F 17/10; G06F 17/2247; G06F 17/24
See application file for complete search history.

(56) References Cited

U.S. PATENT DOCUMENTS 6,820,235 B1 * 11/2004 Bleicher ............... G06F 19/325
715/236
7,054,823 B1 * 5/2006 Briegs ..................... G06F 19/36
705/2

(Continued)

*Primary Examiner* — Miranda Le
(74) *Attorney, Agent, or Firm* — John Maldjian; Maldjian Law Group LLC

(57) ABSTRACT

One example method for predictive clinical planning and design includes instantiating a plurality of data objects, each data object of the plurality of data objects comprising clinical trial information; displaying a graphical user interface on one or more display screens, the graphical user interface providing a graphical representation of at least a portion of a clinical trial and comprising a plurality of graphical nodes; receiving a selection of the second graphical node; receiving, via an editor associated with the second graphical node, a modification of the second data object; propagating an indication of the modification to the first data object, the propagation modifying a clinical trial data item of the first data object; and displaying, within the first graphical node, the modified clinical trial data item of the first data object.

19 Claims, 31 Drawing Sheets

Related U.S. Application Data which is a continuation of application No. 13/925,377, filed on Jun. 24, 2013, now Pat. No. 9,224,224.

(60) Provisional application No. 61/663,292, filed on Jun. 22, 2012, provisional application No. 61/663,057, filed on Jun. 22, 2012, provisional application No. 61/663,299, filed on Jun. 22, 2012, provisional application No. 61/663,398, filed on Jun. 22, 2012, provisional application No. 61/663,219, filed on Jun. 22, 2012, provisional application No. 61/663,357, filed on Jun. 22, 2012, provisional application No. 61/663,216, filed on Jun. 22, 2012.

(51) Int. Cl.
*G06T 11/20* (2006.01)
*G16H 10/60* (2018.01)
*G16H 40/63* (2018.01)
*G16H 10/20* (2018.01)
*G06F 16/248* (2019.01)
*G06F 40/14* (2020.01)
*G06F 40/166* (2020.01)
*G06F 17/10* (2006.01)

(56) References Cited

U.S. PATENT DOCUMENTS

| | | | | |
|---|---|---|---|---|
| 7,594,889 B2* | 9/2009 | St. Ores | | A61B 5/0031 600/301 |
| 7,788,114 B2* | 8/2010 | Mancini | | G06Q 10/10 705/2 |
| 7,899,685 B2* | 3/2011 | Wallach | | G06Q 50/22 705/2 |
| 8,543,603 B2* | 9/2013 | Boris | | G06Q 10/10 705/2 |
| 2003/0060688 A1* | 3/2003 | Ciarniello | | G06Q 40/08 600/300 |
| 2003/0065669 A1* | 4/2003 | Kahn | | G16H 10/20 |
| 2003/0108938 A1* | 6/2003 | Pickar | | G06F 19/3481 435/6.11 |
| 2004/0177090 A1* | 9/2004 | Corbett-Clark | | G06F 16/9024 |
| 2004/0189718 A1* | 9/2004 | Stein | | G06F 19/325 715/853 |
| 2006/0173663 A1* | 8/2006 | Langheier | | G16H 50/20 703/11 |
| 2007/0174252 A1* | 7/2007 | Rawlings | | G06Q 40/08 |
| 2009/0281868 A1* | 11/2009 | Spanbauer | | G06Q 10/0639 705/7.33 |
| 2009/0319535 A1* | 12/2009 | Webber | | G06F 16/252 |
| 2010/0114594 A1* | 5/2010 | Schultz | | G06Q 10/06 705/2 |
| 2010/0228699 A1* | 9/2010 | Webber | | G06F 21/6245 707/622 |
| 2011/0153358 A1* | 6/2011 | Campo | | G06Q 10/06 705/2 |
| 2012/0259647 A1* | 10/2012 | Syed | | G06Q 10/06 705/2 |
| 2012/0290323 A1* | 11/2012 | Barsoum | | G16H 15/00 705/3 |
| 2013/0304504 A1* | 11/2013 | Powell | | G06Q 10/06 705/3 |
| 2015/0007271 A1* | 1/2015 | Wong | | H04L 67/10 726/4 |

* cited by examiner

Objective Associator - EQ-5D  ⊗

⊞ Primary Objectives
☐ 1 To compare different dosing schedules of BIL non-inferiority of HbA1c after 4 months of therapy in T1DM patients; non-inferiority margin (NIM) = 0.4%

⊞ Secondary Objectives
☐ 1 Total and nocturnal hypoglycemia rate
☐ 2 FBG-absolute and chnage from baseline
☐ 3 FBG-intra-subject variability
☐ 4 SMBG (9-point) same problem as above, training point during ISST, multiple time points?
☐ 5 Weight change from baseline
☐ 6 HbA1c change from baseline
☐ 7 Proportion of patients with HbA1c < 7.0%
☐ 8 LY antibodies
☐ 9 Additional safety endpoints
☐ 10 Pharmacokinetics

⊞ Exploratory Objectives

METHODS AND SYSTEMS FOR PREDICTIVE CLINICAL PLANNING AND DESIGN

CROSS-REFERENCE TO RELATED APPLICATIONS

This application is a continuation-in-part of U.S. patent application Ser. No. 14/947,726, entitled "Methods and Systems for Predictive Clinical Planning and Design and Integrated Execution Services," filed Nov. 20, 2015, which is a continuation of U.S. patent application Ser. No. 13/925,377, now U.S. Pat. No. 9,224,224, filed Jun. 24, 2013, entitled "Methods and Systems for Predictive Clinical Planning and Design and Integrated Execution Services," which claims priority to U.S. Provisional Application No. 61/663,292, filed on Jun. 22, 2012, entitled "Method and System to Manipulate Multiple Selections against a Population of Elements;" U.S. Provisional Application No. 61/663,057, filed on Jun. 22, 2012, entitled "Systems and Methods For Predictive Analytics For Site Initiation and Patient Enrollment;" U.S. Provisional Application No. 61/663,299, filed on Jun. 22, 2012, entitled "Methods and Systems for Predictive Clinical Planning and Design and Integrated Execution Services;" U.S. Provisional Application No. 61/663,398, filed on Jun. 22, 2012, entitled "Systems and Methods for Subject Identification (ID) Modeling;" U.S. Provisional Application No. 61/663,219, filed Jun. 22, 2012, entitled "Systems and Methods for Analytics on Viable Patient Populations;" U.S. Provisional Application No. 61/663,357, filed Jun. 22, 2012, entitled "Methods and Systems for a Clinical Trial Development Platform;" U.S. Provisional Application No. 61/663,216, filed Jun. 22, 2012 entitled "Systems and Methods for Data Visualization;" the entirety of all of which are hereby incorporated by reference herein.

FIELD

Examples of the disclosure relate generally to planning, designing, and executing clinical trials. More particularly, examples of the disclosure relate to methods and systems for providing predictive clinical planning and design used in the research and development of pharmaceuticals.

BACKGROUND

A clinical trial is an extremely complicated undertaking. The process normally involves multiple iterations of each stage in the planning, design, execution, and analysis cycle for pharmaceutical development because negative data about the safety or efficacy of the pharmaceutical product will require reformulation, which will then necessitate subsequent small scale trials before larger trials may be attempted.

Before beginning a clinical trial, a significant amount of time and effort is spent in designing the trial. Due to the effort and expense of conducting the trial, it is critical that the trial be designed to be as effective and efficient as possible. This involves gathering and analyzing a large amount of information. Prior art systems attempted to deal with this problem by maintaining information regarding the design of a trial in a multiplicity of documents, such as spreadsheets and word processing documents. However, this approach had problems. For example, if information was captured in one source and needed to be transferred to another source, this had to be done manually. This led to wasted effort, expense, and increased opportunities for errors.

SUMMARY

Examples according to this disclosure provide systems and methods for predictive clinical planning and design. One example method comprises instantiating a plurality of data objects, each data object of the plurality of data objects comprising clinical trial information; displaying a graphical user interface on one or more display screens, the graphical user interface providing a graphical representation of at least a portion of a clinical trial and comprising a plurality of graphical nodes, the plurality of graphical nodes comprising: a first graphical node representing a clinical trial, a second graphical node directly connected to the first graphical node by a graphical connection and representing an aspect of the clinical trial, the second graphical node subordinate in a hierarchy to the first graphical node, and wherein: the first graphical node references a first data object of the plurality of data objects; the second graphical node references a second data object of the plurality of data objects, the second data object references or is referenced by the first data object; at least one of the first or second graphical nodes is associated with an editor configured to enable modification of clinical trial information of one or more of the first or second data objects; receiving a selection of the second graphical node; receiving, via an editor associated with the second graphical node, a modification of the second data object; propagating an indication of the modification to the first data object, the propagation modifying a clinical trial data item of the first data object; and displaying, within the first graphical node, the modified clinical trial data item of the first data object.

These examples are mentioned not to limit or define the disclosure, but to provide examples to aid understanding thereof. Examples are discussed in the Detailed Description, and further description is provided there. Advantages offered by the various examples may be further understood by examining this specification.

BRIEF DESCRIPTION OF THE DRAWINGS

These and other features, aspects, and advantages of the present disclosure are better understood when the following Detailed Description is read with reference to the accompanying drawings, wherein:

FIG. 10 is a diagram illustrating an objectives associator according to one example;

Figure 17:
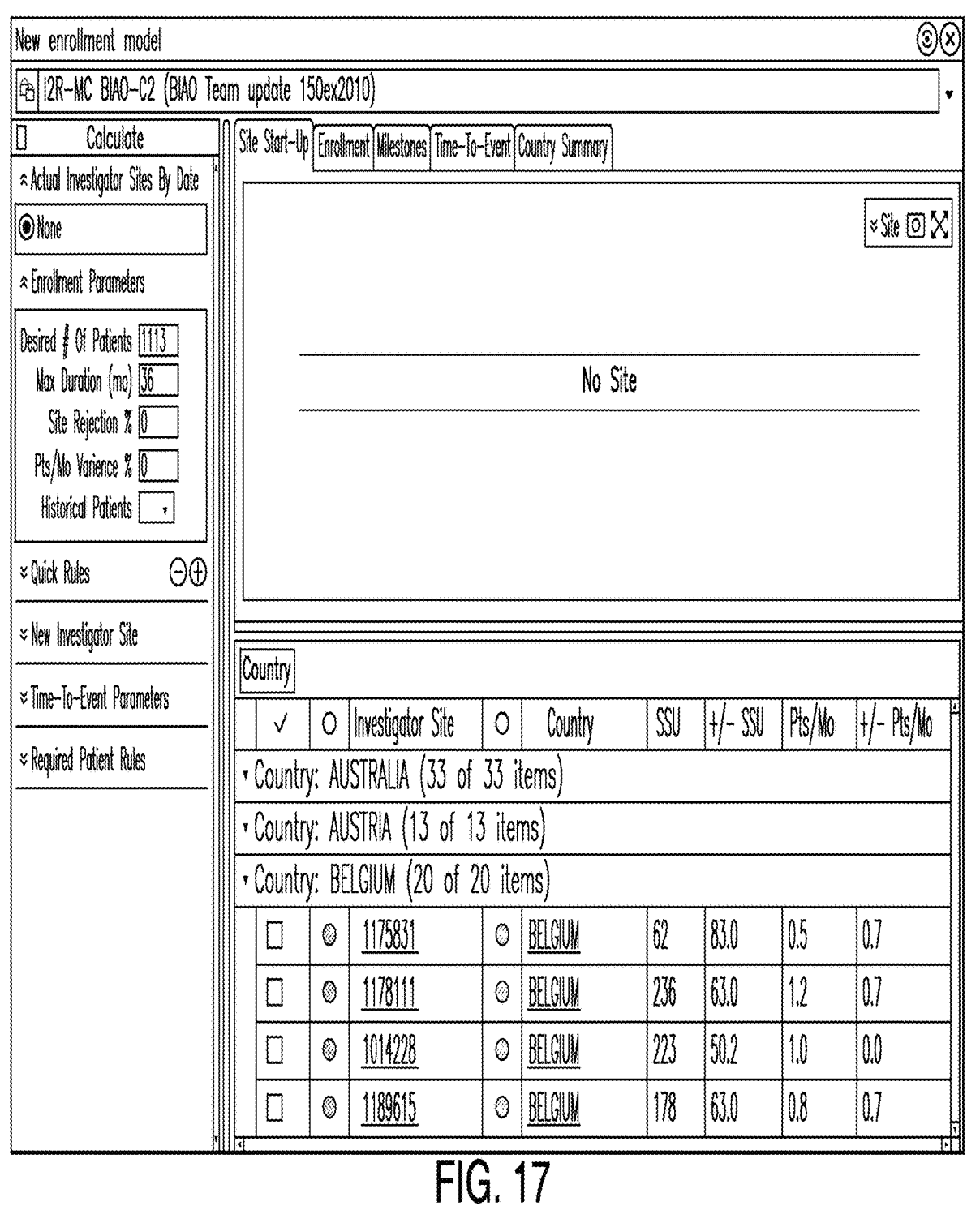

FIG. 17 is a diagram illustrating an enrollment editor according to one example;

Figure 18:
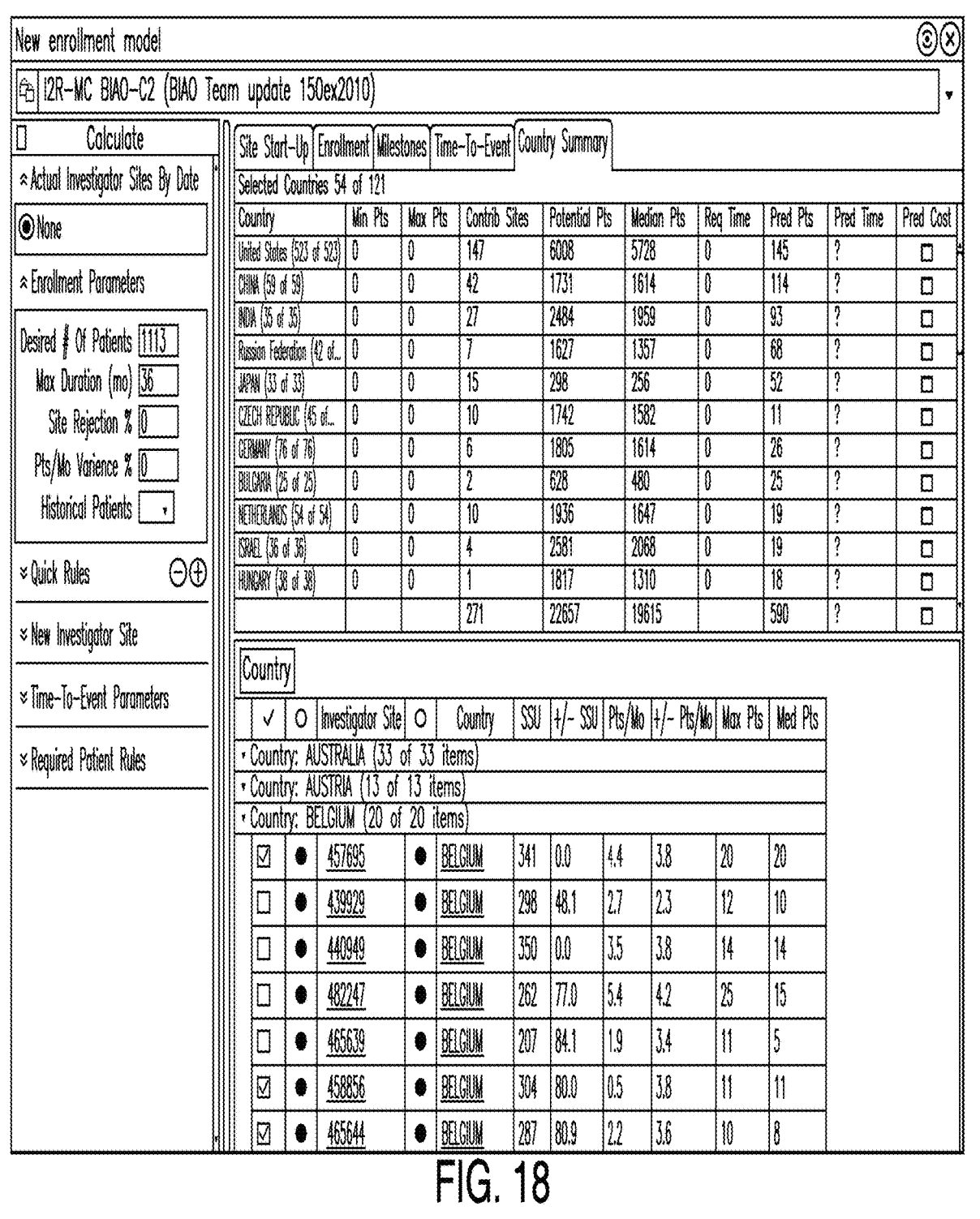

FIG. 18 is a diagram illustrating an enrollment editor according to one example;

DETAILED DESCRIPTION

Figure 1:
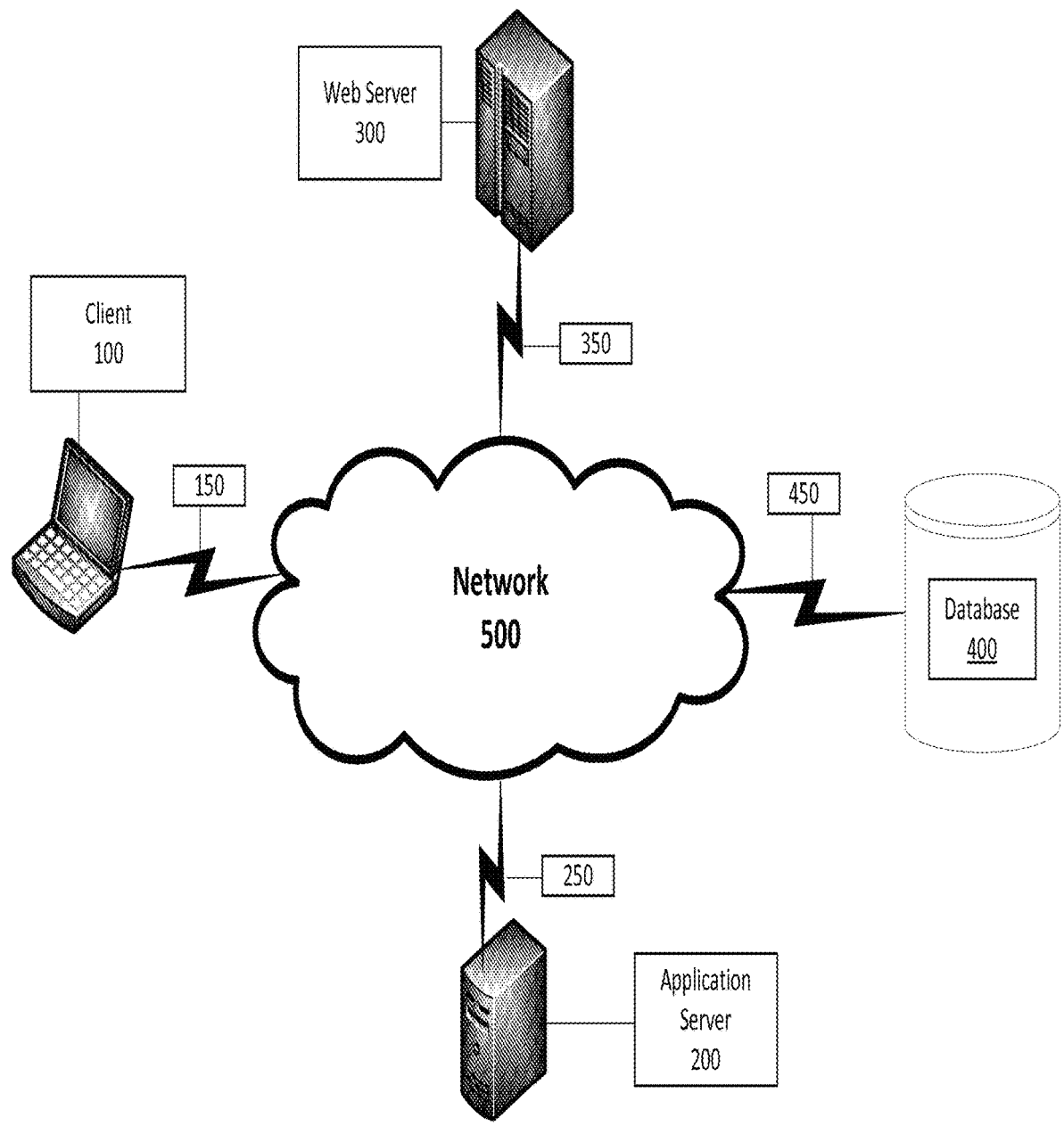
FIG. 1 is a diagram illustrating an exemplary environment for implementation of one example.

Examples according to this disclosure provide systems and methods for predictive clinical planning and design.

Prior to the mass production and sale of a particular pharmaceutical product for the treatment of a medical condition in a human patient, clinical trials are conducted to determine the safety and efficacy of those pharmaceuticals. The clinical trial process requires massive investments of capital, time, and risk. Clinical trials often last periods of months, and frequently years, before a particular pharmaceutical product receives regulatory approval and is deemed effective and safe for the use of the general public.

The clinical trial process is typically carried out by multiple teams of investigators and researchers spread over a significant geographic area. This is often necessary because of the number of volunteer subjects required to obtain useful data on the safety and efficacy of the pharmaceutical product. Large populations are needed to obtain valid data because data tends to be more statistically reliable when sample sizes are larger; volunteers of varying demographics ensure that the pharmaceutical product works consistently and predictably across different demographics; it is challenging to secure the commitment of reliable volunteer subjects; and regulations require that the pharmaceutical be tested over a wide number of volunteer subjects to minimize any doubts regarding safety and efficacy.

Consequently, clinical trials are logistically and administratively demanding. It is difficult to coordinate and exchange information between teams of investigators. The information systems used by clinical trial teams vary, and the transfer of data from one stage of a clinical trial to the next is error-prone, costly, and repetitive. Furthermore, it is challenging to alter the specifications of the clinical trial plan and subsequently predict how those changes will impact the cost, accuracy, and logistical difficulty of the trial.

Examples according to this disclosure provide systems and methods for clinical program management. In some examples, the method comprises one or more users developing a strategic map of a proposed clinical plan. The clinical plan may comprise one or more of: a draft launch label attribute, one or more strategies, and a schema. In some examples, the method also comprises linking the clinical plan and schema to one or more trials. The method may also comprise subsequently linking the trials to one or more objectives and measures. Further, the method may also comprise subsequently linking none, one, or a plurality of objectives to none, one, or a plurality of measures. In some examples, the method further comprises identifying patient criteria. The method may also comprise enrolling patients from one or more investigator sites. The investigator sites may be located in one or more countries. The method may also comprise integrating the clinical plan with a clinical plan execution application.

Some examples provide a schema designer. The schema designer may provide a means by which a user can perform one or more of the following: enter data related to a clinical trial, view a visualization of the events comprising that clinical trial, identify constraints that are being met (or not being met), and make changes to the clinical trial. In some examples, the system graphically displays all of the information entered regarding the clinical trial. In other examples, a logically-grouped subset of information is provided. Further, as new data is entered into the system, the graphic representations may be automatically and dynamically updated such that any user in any location may access and view the updated graphic representations.

Some examples also provide a digital design canvas which facilitates the planning, design, and adjustment of a clinical trial. The canvas may allow a user to create, access, and alter protocol elements of a clinical trial without the need to manually re-enter information across disparate systems or formats. In some examples, the canvas integrates the schema and the schedule of events for a clinical trial such that changes to either are automatically reflected in the other. To provide such features, the canvas may interact with an object graph that stores information about various aspects of the clinical trial. Each object in the object graph may represent a node in the graph, while relationships or references between objects may represent the edges. Such nodes and edges may correspond to one or more graphical nodes and edges, but may not have a 1-to-1 correspondence in some examples.

Referring now to the drawings, in which like numerals indicate like elements throughout the several figures, FIG. 1 is a diagram illustrating an exemplary environment for implementation of one example according to this disclosure. The example shown in FIG. 1 includes a client 100 that allows a user to interface with an application server 200, web server 300, and/or database 400 via a network 500.

The client 100 may be, for example, a personal computer (PC), such as a laptop or desktop computer, which includes a processor and a computer-readable media. The client 100 also includes user input devices, such as a keyboard and mouse or touch screen, and one or more output devices, such as a display. In some examples according to this disclosure, the user of client 100 accesses an application or applications specific to one example according to this disclosure. In other examples, the user accesses a standard application, such as a web browser on client 100, to access applications running on a server such as application server 200, web server 300, or database 400. For example, in one example, in the memory of client 100 are stored applications including a design studio application for planning and designing clinical trials. The client 100 may also be referred to as a terminal in some examples according to this disclosure.

Such applications may be resident in any suitable computer-readable medium and executable on any suitable processor. Such processors may comprise, for example, a microprocessor, an ASIC, a state machine, or other processor, and can be any of a number of computer processors, such as processors from Intel Corporation, Advanced Micro Devices Incorporated, and Motorola Corporation. The computer-readable media stores instructions that, when executed by the processor, cause the processor to perform the steps described herein.

The client 100 provides a software layer, which is the interface through which the user interacts with the system by receiving and displaying data to and from the user. In one example, the software layer is implemented in the programming language C #. In other examples, the software layer can be implemented in other languages, such as Java or C++. The software layer may include a graphical user interface and use visual representations of data to communicate said data to one or more users. The visual representations of data may also be used to receive additional data from one or more users. In one example, the visual representation appears as a spider-like layout of nodes and connectors extending from each node to a central node.

Examples of computer-readable media comprise, but are not limited to, an electronic, optical, magnetic, or other storage device, transmission device, or other device that comprises some type of storage and that is capable of providing a processor with computer-readable instructions. Other examples of suitable media comprise, but are not limited to, a floppy disk, CD-ROM, DVD, magnetic disk, memory chip, ROM, RAM, PROM, EPROM, EEPROM, an ASIC, a configured processor, all optical media, all magnetic tape or other magnetic media, or any other medium from which a computer processor can read instructions. Also, various other forms of computer-readable media may be embedded in devices that may transmit or carry instructions to a computer, including a router, private or public network, or other transmission device or channel, both wired and wireless. The instructions may comprise code from any suitable computer-programming language, including, for example, C, C++, C #, Visual Basic, Java, Python, Perl, and JavaScript.

The application server 200 also comprises a processor and a memory. The application server may execute business logic or other shared processes. The application server may be, for example, a Microsoft Windows Server operating in a .NET framework, an IBM Weblogic server, or a Java Enterprise Edition (J2E) server. While the application server 200 is shown as a single server, the application server 200, and the other servers 300, 400 shown may be combined or may include multiple servers operating together to perform various processes. In such examples, techniques such as clustering or high availability clustering may be used. Benefits to architectures such as these include redundancy and performance, among others.

In the example shown in FIG. 1, the application server 200 is in communication with a web server 300 via a network connection 250. The web server 300 also comprises a processor and a memory. In the memory are stored applications including web server software. Examples of web server software include Microsoft Internet Information Services (IIS), Apache Web Server, and Sun Java System Web Server from Oracle, among others.

In the example shown in FIG. 1, the web server 300 is in communication with a database 400 via a network connection 350 and a network connection 450. The web server 300 provides a web service layer that, together or separate from application server 200, acts as middleware between a database 400 and the software layer, represented by the client 100. The web server 300 communicates with the database 400 to send and retrieve data to and from the database 400.

The network 500 may be any of a number of public or private networks, including, for example, the Internet, a local area network ("LAN"), or a wide area network ("WAN"). The network connections 150, 250, 350, and 450 may be wired or wireless networks and may use any known protocol or standard, including TCP/IP, UDP, multicast, 802.11b, 802.11g, 802.11n, or any other known protocol or standard. Further, the network 100 may represent a single network or different networks. As would be clear to one of skill in the art, the client 100, servers 200, 300, and database 400 may be in communication with each other over the network or directly with one another.

The database 400 may be one or a plurality of databases that store electronically encoded information comprising the data required to plan, design, and execute a clinical trial. In one example, the data comprises one or more design elements corresponding to the various elements related to one or more clinical trials. The database 400 may be implemented as any known database, including an SQL database or an object database. Further, the database software may be any known database software, such as Microsoft SQL Server, Oracle Database, MySQL, Sybase, or others.

Figure 2:
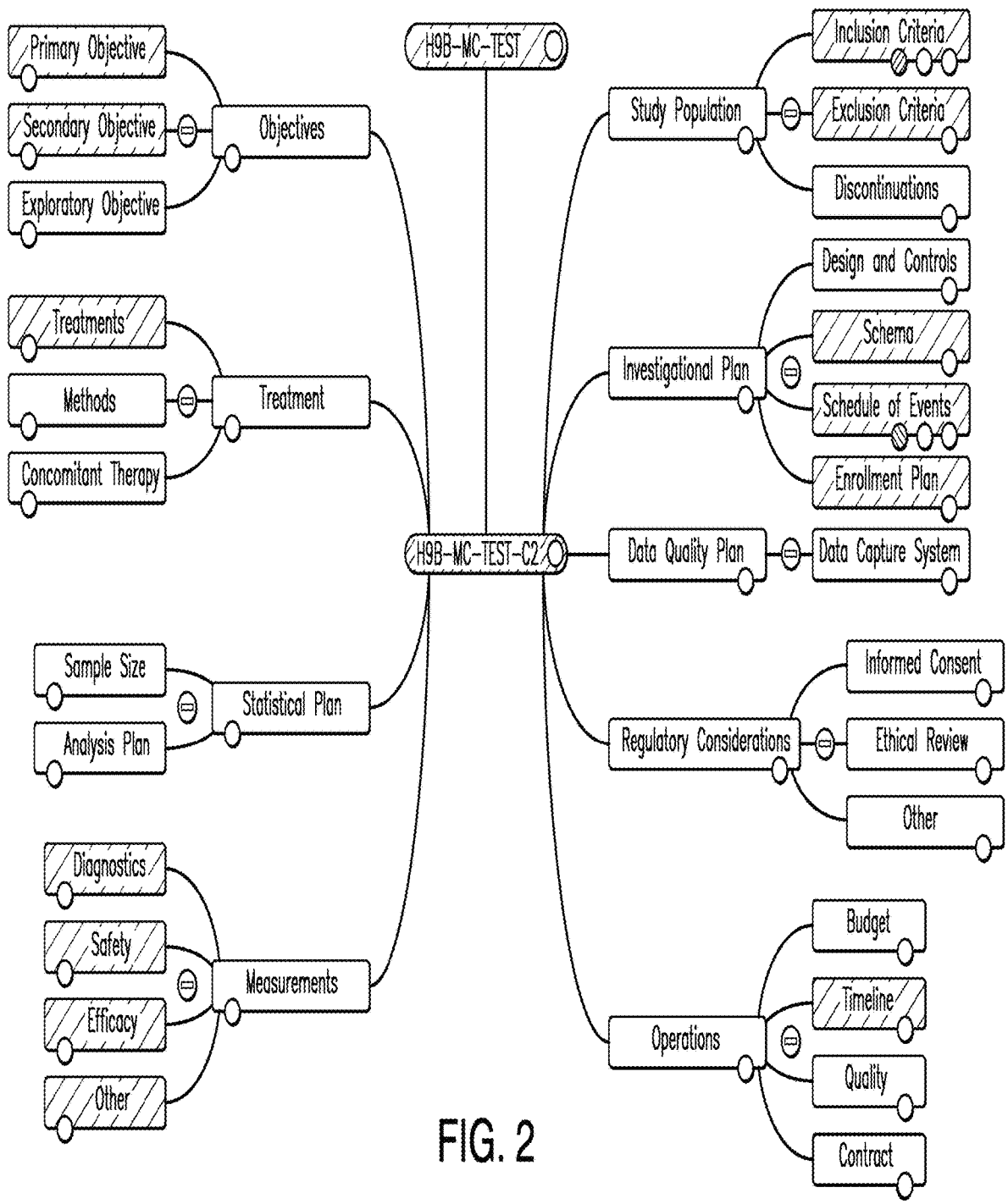
FIG. 2 is a diagram illustrating a context map according to one example.

FIG. 2 is a diagram illustrating a context map according to one example. A context map is a representation of the bounded contexts involved in a project and the actual relationships between them and their models. For example, the context map in FIG. 2 depicts the relationships of the objectives associated with a clinical trial. In this example, the context map is depicted as a hierarchical arrangement of nodes and sub-nodes, each of which will be discussed in more detail. The nodes and sub-nodes may be connected to each other via relationships defined in software objects underlying the graphically-represented nodes. Some of these relationships may be visually depicted, while others may be implicitly represented by changes made in one node affecting the state of another node.

FIG. 2 is described herein in reference to the illustrative environment shown in FIG. 1. However, the process is not limited to execution within that environment. In one example, a context map, as shown in FIG. 2 is generated by the application server 200 and displayed on the client 100.

As shown in FIG. 2, the context map includes multiple nodes, each of which represents a design element. In one example, the context map includes an objectives node, a treatment node, a statistical plan node, a measurements node, a study population node, an investigational plan node, a data quality plan node, a regulatory considerations node, and/or an operations node.

In the example shown in FIG. 2, the context map includes one or more sub-nodes extending from each node. For example, the objectives node includes a primary objective sub-node, a secondary objective sub-node, and an exploratory objective sub-node. A user who is viewing and interacting with the context map via the client 100 may then use the sub-nodes to enter information regarding the primary objective(s), secondary objective(s), and/or any exploratory objective(s). Correspondingly, the user may enter information regarding other sub-nodes as well. It should be appreciated that the distinction between a "node" and a "sub-node" is merely for purposes of easily distinguishing different levels of hierarchy within this description. In some examples, however, each graphical element of the context map may be referred to as a node or a sub-node depending on the context.

In various examples, using a context map, such as the one disclosed in FIG. 2, provides significant flexibility to the individual(s) designing a clinical trial. For example, during the early stage of trial design, the information entered may be very high level. At such a stage, the designer(s) may have a rough idea of the inclusion and exclusion criteria for the study population and may thus enter the information in the inclusion criteria and/or exclusion criteria sub-nodes of the study population node.

In one example, when a user selects a particular node or sub-node, graphic representations appear primarily as either dashboards or editors that are configured to receive and present data to one or more users. In various examples, dashboards provide representations of various sets of data within the system. Selecting a node in a dashboard will launch a corresponding editor. Editors comprise interfaces through which one or more users inputs design parameters which are combined with proprietary and outsourced data and then displayed as graphs to show the impact of user choices.

In one example, a graphic representation may consist of menus and text entry fields from which one or more users may instantiate a clinical trial by selecting an existing molecule or entering a new molecule candidate. In some examples, an existing molecule or a new molecule candidate is a chemical compound used for pharmaceutical treatment, or a proposed chemical compound intended to be used for pharmaceutical treatment. Additional information may be entered from this graphic representation, for example candidate details such as a display name, full title, candidate names, disease indication or indications, and phase of development.

In one example, a graphic representation may consist of images, symbols, and text arranged in panels and panes to provide one or more users the ability to search through information pertaining to clinical trials stored within the system. Panels and panes may consist of, for example, catalogs, search panels, and design canvases. A catalog comprises an interface where shortcuts to access molecules, clinical plans, and trial candidates may be selected to launch corresponding dashboards and editors or to display schemas of selected trial candidates in the design canvas. A search panel comprises an interface that may be used to reduce the number of trial candidates displayed in the design canvas according to selected trial facets. A design canvas comprises the representation of information such as dashboards and editors or to display schemas of selected trial candidates requested by the user or a plurality of users. In some examples, a design canvas may comprise the output of a faceted search.

As discussed above, the nodes may represent aspects of one or more clinical trial designs being created or edited within the system. Each node may provide a graphical indication of the current state of the respective information associated with the node, and may also be used to adjust parameters of the clinical trial through an editor associated with the node. In some examples, interconnections between the nodes may represent a causal relationship between information contained within different nodes. For example, the Predictive Analytics node, which has an "Enrollment Plan" sub-node, may graphically provide information about an investigational plan based on information that has been entered in the Enrollment Plan node.

For example, a user may access the Enrollment Plan node, such as by selecting it with a mouse cursor, and then access an editor associated with the Enrollment Plan node. The user may then add, change, or delete information within the Enrollment Plan node. Those modifications to the information accessible through the Enrollment Plan node may then affect information presented in the Investigational Plan node. Thus, the context map, and its interconnected nodes and sub-nodes, may enable a clinical trial designer to iteratively adjust information within the context map to determine its effect on the proposed trial design.

In some examples, data referenced by one or more nodes may be represented in software by one or more data objects instantiated by the system. Such data objects may include clinical trial data represented by one or more clinical trial data items, one or more methods to provide behavior for the object, or one or more references to other data objects. Thus, data referenced by a node may be stored in one or more interconnected software-implemented data objects. When interacting with an editor associated with a node, the user may edit data associated with the node, which may then be stored within one or more of these data objects.

Further, because the data objects may be interconnected, changes made in the editor may trigger behavior in one or more of these objects, or may cause data objects that were not directly modified through the editor to be impacted, such as through one or more methods called by a modified data object, or by explicit calls to such data objects from the graphical node, such as in response to a user pressing a "save" button. Such interconnections and inter-object communication may enable changes made in an editor for one node to propagate through to affect information represented in another node or nodes. For example, modifications made in the Enrollment Plan node may affect the Investigational Plan, such as by increasing the cost of the investigational plan, e.g., due to an increased enrollment period or a decreased number of enrollment sites.

In this example, the nodes have been arranged in a particular hierarchy, however, in some examples, the hierarchy may be customized by the user as she edits the clinical trial. For example, connections between nodes may be modified to adjust the hierarchy or to adjust propagation of data values from one node to another. For example, a user may select a node and then select an option to create, modify, or delete a connection to another node. The user may then identify the other node with which the connection should be created, modified, or deleted. Thus, in some examples, each individual node may be viewed as a discrete component that may be "plugged into" the clinical trial according to the particular requirements of the user editing the clinical trial, rather than requiring a particular hierarchy or paradigm for the clinical trial.

In addition to adjusting connections between nodes, or the location of a node within the clinical trial schema, with respect to each individual connection, the user may select data that may propagate through the connection to another node, and the direction in which the data should propagate. For example, a user may select a data item in one graphical node, the source graphical node, and then select a second graphical node to propagate the data item to the destination graphical node. After selecting the data item and the destination node, the user may then establish how the propagation should occur. For example, the user may select a data item in the destination graphical node and indicate that the two data items should be compared or added together.

In some examples, the user may identify a precondition associated with the data item to be propagated. For example, the user may indicate that the destination node may indicate an error if the precondition is not met. For example, if a patient population is to be propagated to a scheduling node, the user may establish a precondition indicating a required minimum patient population before scheduling activities may be determined.

Thus, the user may customize the flow of data through the clinical trial plan, which may then enable the user to create or modify dependencies within the clinical trial.

After creating a connection between two nodes and identifying which data may pass along the connection, the user may then, using the respective editor for the node that receives the data, specify how the data is to be integrated into the node. For example, the editor may enable the new data to be used as a constraint on functionality provided in the receiving node or as a sub-component of a higher-level item, such as an input to a costing function or a scheduling function.

Using such a customizable design, a user may flexibly design a clinical trial that reflects the user's particular requirements. Further, the user may employ the customized design to iterate through different assumptions or inputs into the clinical trial to assess their impact on the proposed clinical trial design and whether the proposed design conforms to the requirements from the sponsor of the clinical trial.

It should be appreciated that while the foregoing description of the data objects has referred to the data as being represented in an object-oriented paradigm, other software design techniques may be used instead.

Figure 27:
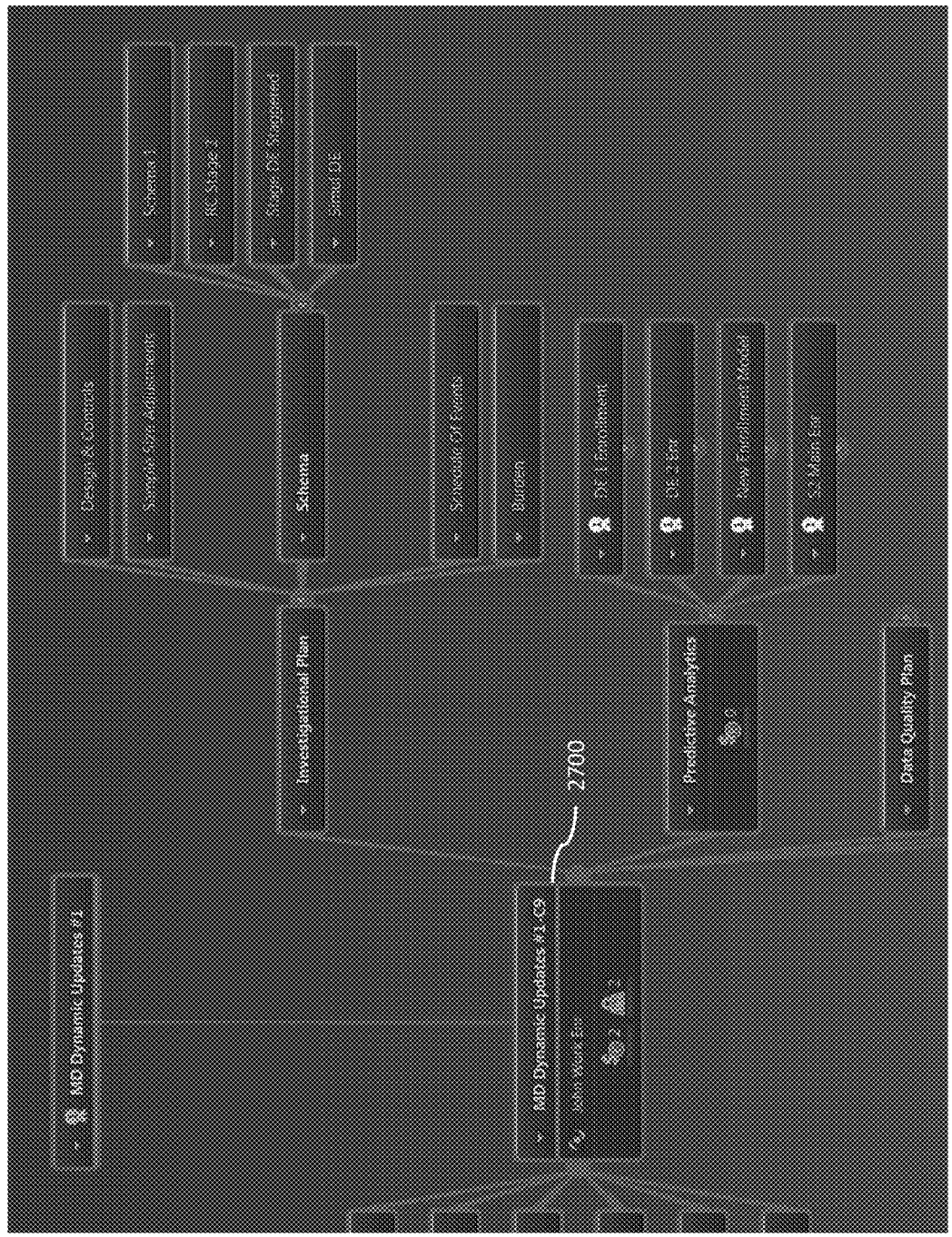
FIG. 27 is an example GUI having a plurality of graphical nodes.

In addition to customizing connections and data propagation between graphical nodes, within an editor for a particular node, the user may customize connections between data items of data objects referenced by the particular graphical node. For example, referring to FIG. 27, FIG. 27 shows an example GUI having a plurality of graphical nodes as discussed above. In this example, a user may select a graphical node 2700 and activate an editor associated with it.

Figure 28:
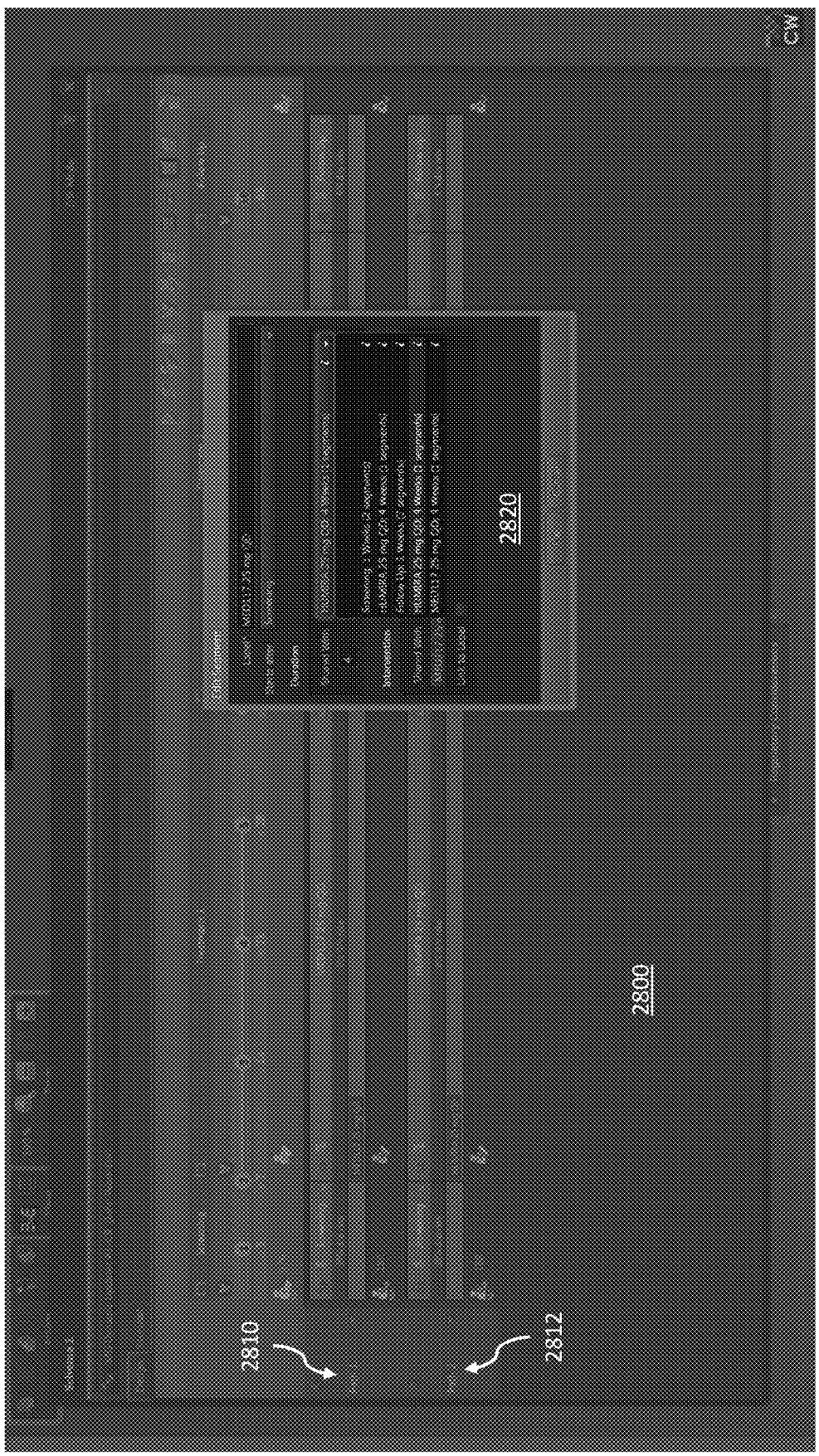
FIG. 28 shows an editor associated with a selected graphical node.

Referring now to FIG. 28, an editor 2800 associated with the selected graphical node 2700 has been launched, which provides the user with an option to establish different patient paths 2810-12 within a clinical trial. In this example, each patient path 2810-12 is associated with its own respective data objects that store information associated with the respective patient path 2810-2812. In addition, the user has opened an option window 2820 for a first one of the patient paths 2810. As can be seen in the option window, various aspects of the path 2810, such as a segment of the path, can be seen or edited within the option window 2820.

Figure 29:
FIGS. 29-31 show example option windows providing option to share data items.

Referring now to FIG. 29, in this example, the option window 2820 provides an option for sharing data items from the first patient path 2812. As can be seen in this example, the "Duration" data item 2910 and the "Intervention" data item 2912 are both shared with the second patient path 2812.

Figure 30:

Referring now to FIG. 30, in this example, the option window 3000 for the second patient path 2812 is shown and illustrates that the values for Duration and Intervention data items 3010-12 have received data shared from the first patient path 2810. Thus, while the Duration and Intervention data items 3010-12 reflect values stored in the data objects associated with the second patient path 2812, they have been populated with the values shared from the first patient path 2810.

Figure 31:

Referring now to FIG. 31, the user has now employed the option window 3000 for the second patient path 2812 and has eliminated the data sharing between the first and second patient paths 2810-12 and has entered a value of 5 weeks for the Duration data item 3010. Thus, a user may selectively establish or eliminate relationships between data objects associated with an individual graphical node.

Figure 3:
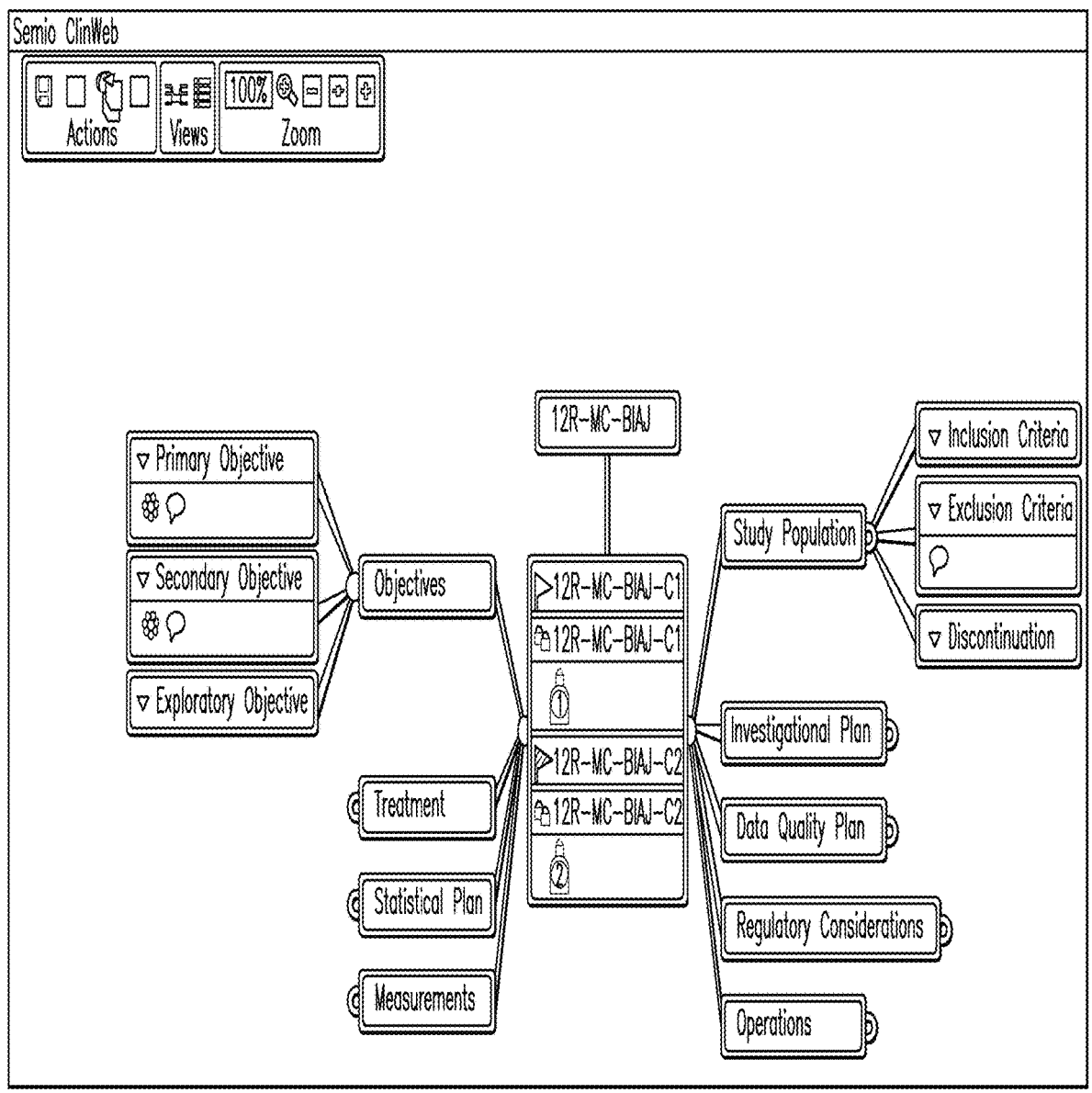
FIG. 3 is a diagram illustrating a trial comparator according to one example.

FIG. 3 is a diagram illustrating a trial comparator according to one example. There can be a benefit to comparing multiple trial candidates and identifying which elements of the candidates differ. This allows a user to quickly identify the differences and can help in determining which trial to pursue or whether to make changes to a candidate. In some examples, a graphical representation comprising a trial comparator that graphically overlaps selected trial candidates is provided. In some examples, the trial comparator visually indicates, with a haloing or highlighting effect, which elements of the selected trials differ. This is shown in FIG. 3, where the primary objective, secondary objective, and exploratory objectives are haloed, as well as the exclusion criteria. In some examples, the trial comparator is accessed by selecting trial candidates from a catalog and selecting a trial comparator button.

The trial comparator in this example, provides multiple nodes, as discussed above, arranged in a hierarchical relationship. Each of these nodes may reference one or more interconnected data objects and obtain data from those objects to generate information to display within the trial comparator. For example, a node may provide summary information that is derived from data stored in objects associated with the node or nodes dependent from the node, or based on nodes higher in the hierarchy than the node. As discussed above, data may propagate between different data objects according to their respective interconnections, which may or may not correspond to the graphical hierarchy of nodes within the clinical trial.

Figure 4:
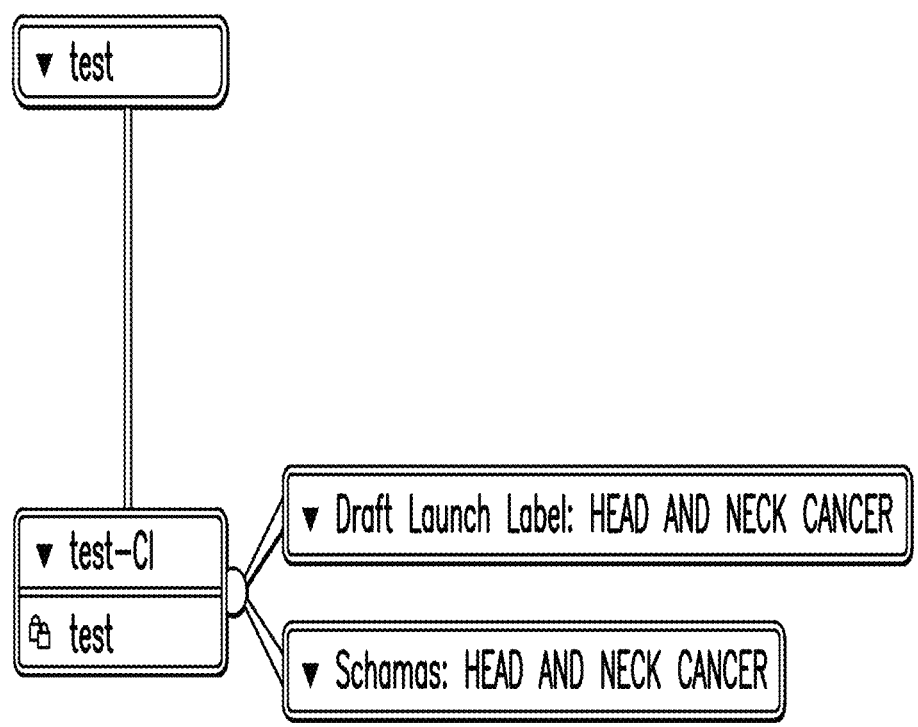
FIG. 4 is a diagram illustrating a clinical plan dashboard according to one example.

FIG. 4 is a diagram illustrating a clinical plan dashboard according to one example. In order to create a clinical plan schema, some examples provide a clinical plan dashboard which allows a user to select a schema in order to open for viewing or editing. In the example illustrated in FIG. 4, a clinical plan dashboard comprises nodes configured to launch dashboards and editors for creating clinical plan schemas and strategies. In some examples, nodes in a clinical plan dashboard for which data has not been entered are highlighted in some manner. An example is shown in FIG. 4, where the DLL and schemas nodes are gray which indicates that the data corresponding to the DLL and schemas has not yet been entered.

Figure 5:
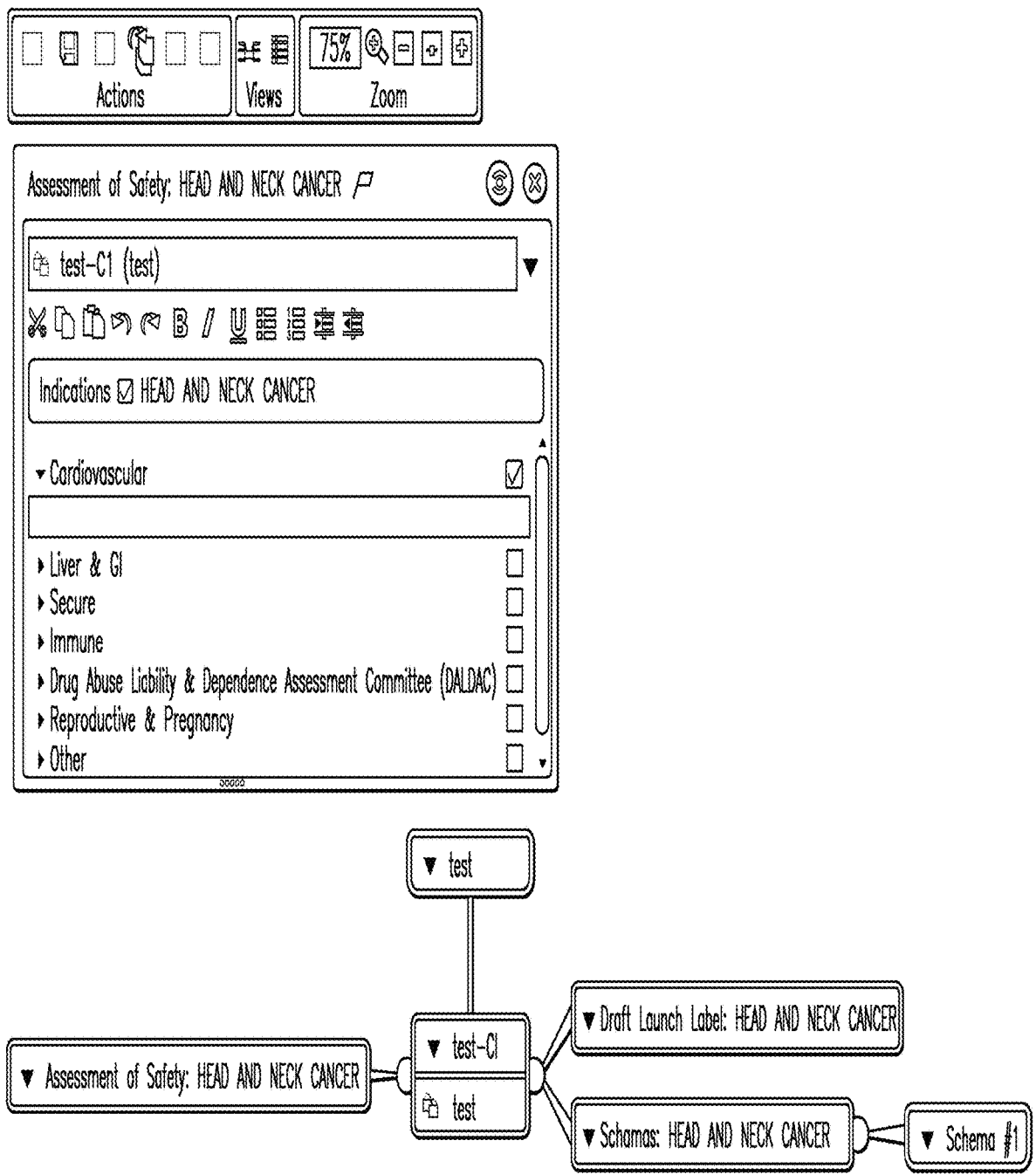
FIG. 5 is a diagram illustrating a strategy editor according to one example.

FIG. 5 is a diagram illustrating a strategy editor according to one example. In some examples, a strategy editor comprises an already created schema and associated information, and is configured to allow one or more users to enter additional data relating to a specific strategy. The example depicted in FIG. 5 illustrates a strategy editor that is configured to enter data corresponding to the assessment of safety strategy for a particular schema. A specific strategy editor may be instantiated by selecting a particular node from a clinical plan dashboard.

Figure 6:
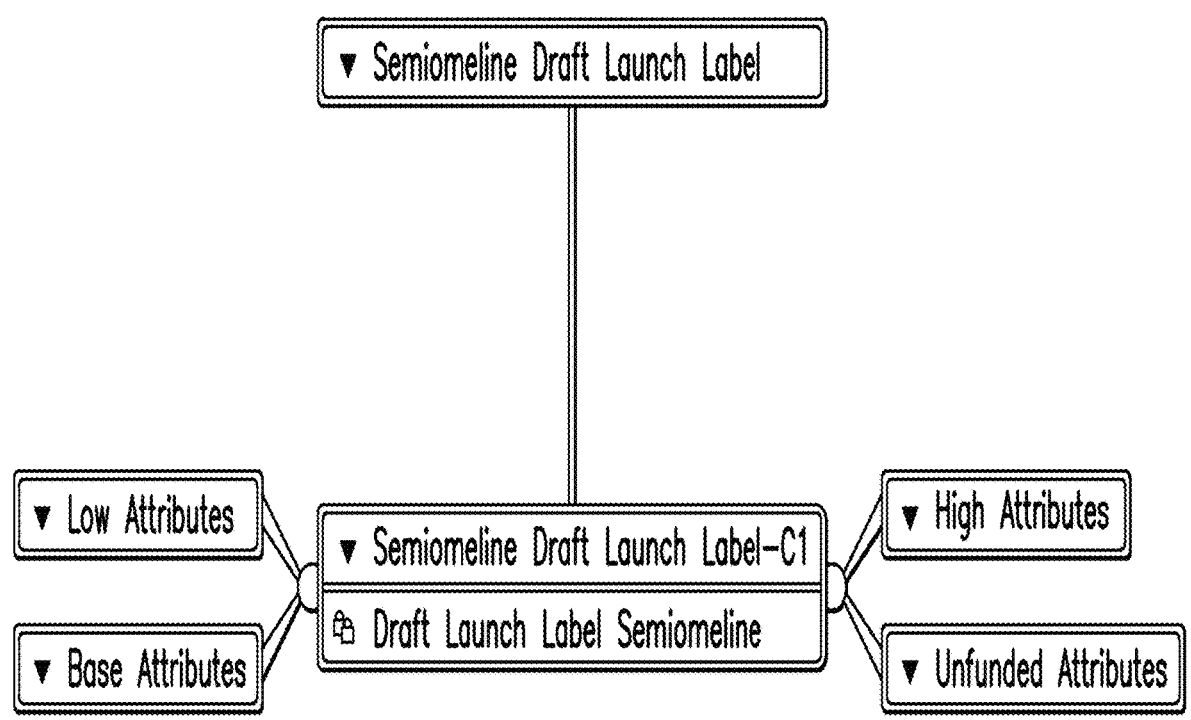
FIG. 6 is a diagram illustrating a draft launch label (DLL) dashboard according to one example.

FIG. 6 is a diagram illustrating a draft launch label (DLL) dashboard according to one example. In various examples, a DLL comprises multiple informational attributes, including low, high, base, and unfunded attributes. Low attributes comprise requirements of a particular clinical plan, base attributes comprise the most likely outcomes of a clinical plan, and high attributes comprise the most favorable outcomes of a clinical plan. In some examples, each attribute type is represented graphically by a node on the DLL dashboard. One or more users may select a node from a DLL dashboard to launch a corresponding editor to enter data for a particular attribute.

In one example, as illustrated in FIG. 6, a DLL dashboard includes a main node (in one example titled Semiomeline Draft Launch Label), a candidate node below the main node (in one example titled Semiomeline Draft Launch Label-Cl), and four attribute type nodes linked to the main node (in one example titled Low Attributes, Base Attributes, High Attributes, and Unfunded Attributes).

Figure 7:
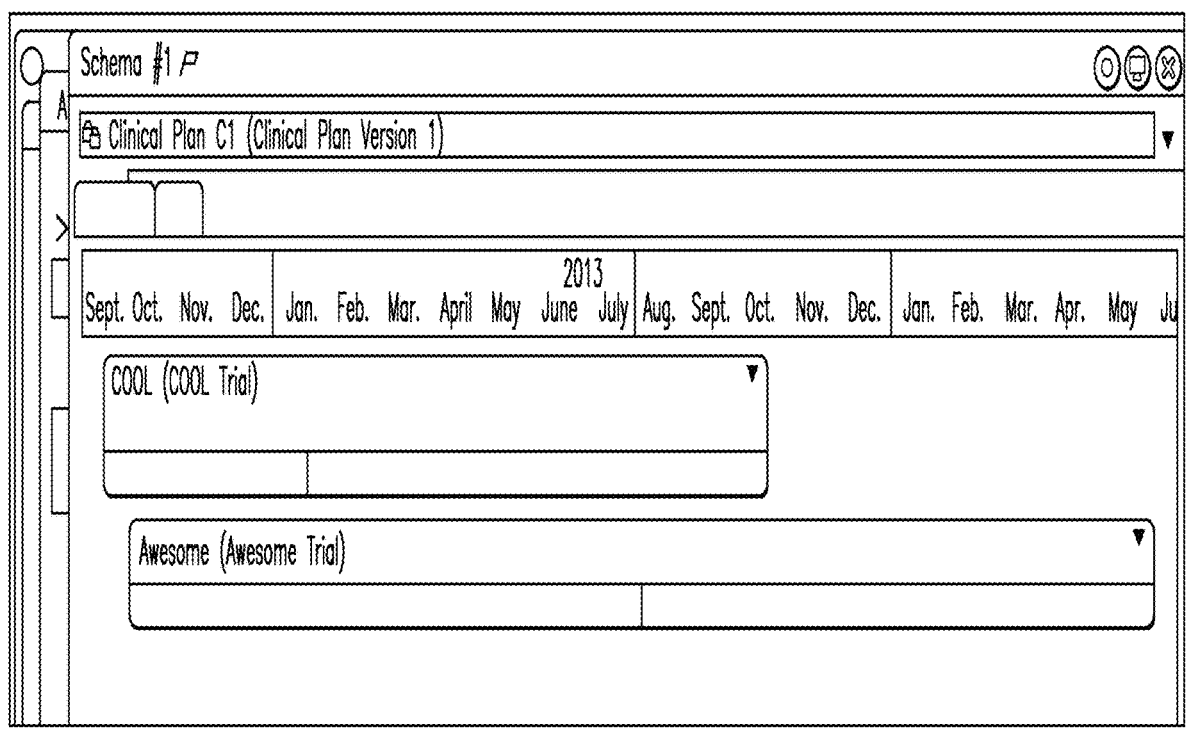
FIG. 7 is a diagram illustrating a clinical plan (CP) schema according to one example.

FIG. 7 is a diagram illustrating a clinical plan (CP) schema according to one example. In some examples, a CP schema comprises a visual timeline representation of the trials and milestones associated with a CP candidate. A CP schema may comprise one or more trials. For example, in the example illustrated in FIG. 7, there are two trials: one named "COOL" and another named "Awesome." In such an example, a trial dashboard may be instantiated by selecting it within a relevant CP schema. Thus, if a user selected "COOL," then the "COOL" trial dashboard would be launched. Correspondingly, if a user selected "Awesome," then the "Awesome" trial dashboard would be launched. Trials may be added to a CP schema by a user by selecting a button within the user interface.

Figure 8:
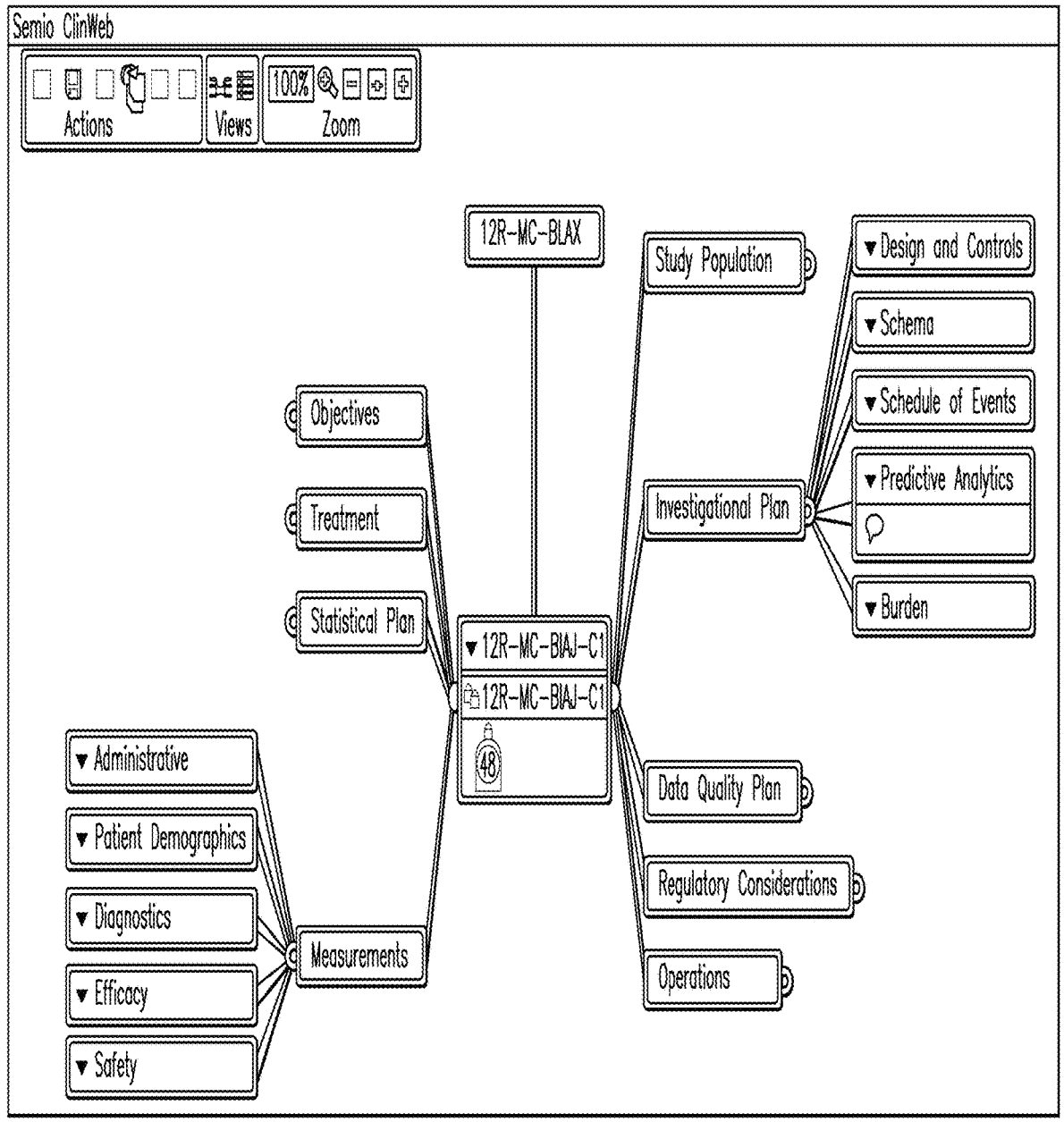
FIG. 8 is a diagram illustrating a trial dashboard according to one example.

FIG. 8 is a diagram illustrating a trial dashboard according to one example. In some examples, a trial dashboard comprises one or more nodes. The one or more nodes may correspond to editors and a predictive analytics dashboard, a main node, a candidate node, a plurality of nodes linked to the candidate node, and/or information depicting the predicted cost and patient burden of the trial candidate. In the example illustrated in FIG. 8, a patient burden of 48 is shown below the candidate node. A patient burden is a value that represents the amount of burden that a particular test will place on a patient. For example, events such as a blood draw or a biopsy would yield a higher burden score, while merely filling out a short survey would yield a lower burden score.

In some examples, one or more nodes correspond to editors. When such a node is selected, this causes an editor to launch. An editor may allow a user to enter data. Examples of such data may include one or more of: objectives, treatments, diagnosis measures, efficacy measures, patient selection, enrollment, patient visit schedules, and trial candidate schemas.

In some examples, a graphic representation comprises an objectives editor. An objectives editor comprises a means by which a user may define trial candidate objectives. In some examples, each objective comprises text and association fields configured to indicate that the objective is associated with a measure.

In some examples, a graphic representation comprises a diagnostics editor. A diagnostics editor comprises a means by which one or more users may define and select diagnosis measures. A diagnostics editor may be instantiated from the schedule of events.

Figure 9:
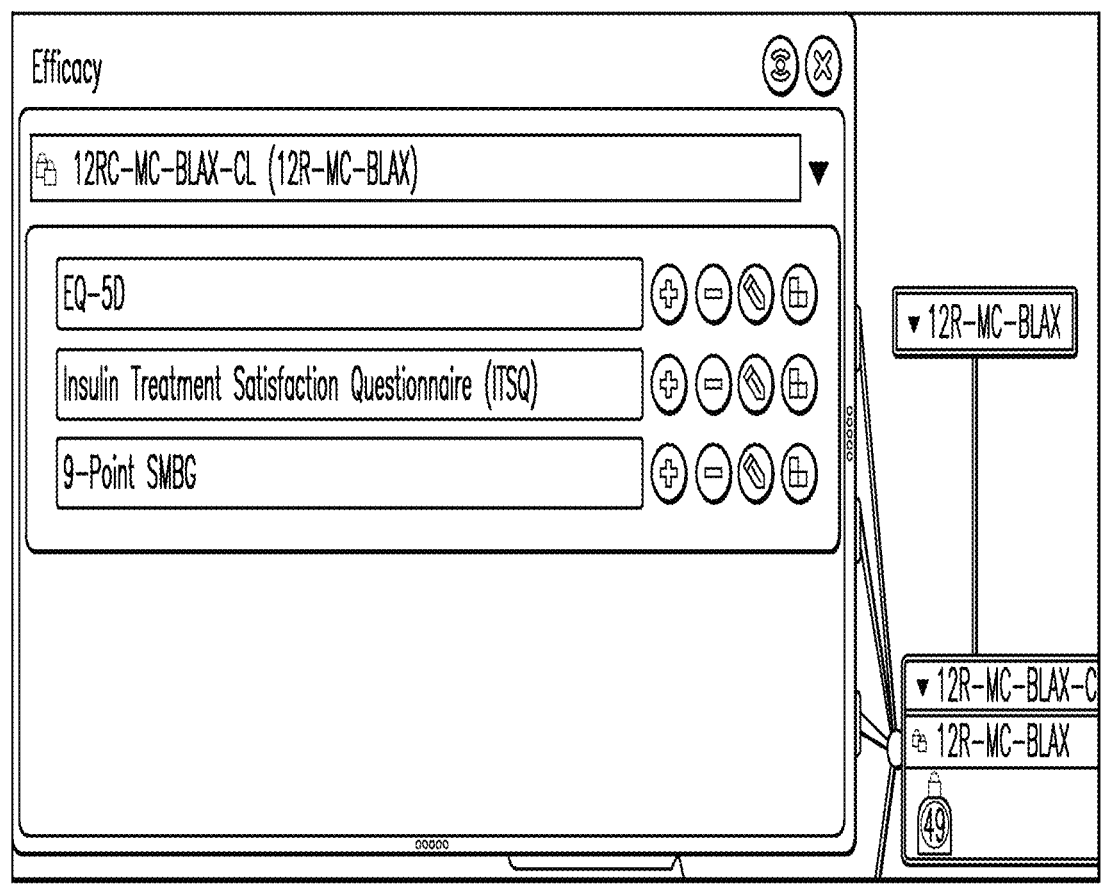
FIG. 9 is a diagram illustrating an efficacy editor according to one example.

FIG. 9 is a diagram illustrating an efficacy editor according to one example. In some examples, an efficacy editor comprises a means by which one or more users may define efficacy measures and associations. In the example illustrated in FIG. 9, an efficacy editor includes a table of measures (including in one illustrative example: EQ-5D, Insulin Treatment Satisfaction Questionnaire, and 9-point SMBG) and buttons configured to attach case report forms (CRFs) and associate objectives.

In some examples, after a CRF or objective is associated, the corresponding button changes color. Accordingly, by observing the table, a user can assess the overall status of the efficacy measures design.

Additionally, the efficacy editor may include an objective associator button. This button may be located beside the measure. In the example illustrated in FIG. 9, an objective associator button is located to the right of each measure. For example, if a user clicked the objective associator button to the right of the EQ-5D measurement, the EQ-5D objective associator would be launched. When an efficacy measure is associated with an objective, this aggregates efficiency measurement resources invested to achieve the objective. However, in some instances no objective is associated with an efficiency measure. In such a case, it may be determined that such a measure is not necessary.

FIG. 10 is a diagram illustrating an objectives associator according to one example. In some examples, an objectives associator comprises a means by which one or more users may associate objectives with efficacy measures. As discussed in the context of the example illustrated in FIG. 9, if a user clicks the objectives associator button associated with a measurement in the efficacy editor, then the objectives associator is launched. In the example illustrated in FIG. 10, a user has clicked the objective associator next to EQ-5D and as a result the objectives associator for EQ-5D was launched. In some examples, the objectives associator comprises a list of objectives and corresponding association buttons. In the example illustrated in FIG. 10, the objectives associator includes a primary objective and a list of ten secondary objectives. In some examples, selecting an association button associates the corresponding objective with the efficacy measure from which the associator was instantiated.

Also, in some examples the objectives associator provides an indication when an efficacy measure and its corresponding objective have been associated. For example, in one example the objectives associator button shows a checkmark and the objective selection button in the efficacy editor is colored blue to visually indicate an association.

In some examples, a graphic representation may comprise a study population editor. A study population editor comprises a means by which one or more users may input population inclusion and exclusion data. In some examples, a study population editor comprises drop-down menus and text fields for inputting data.

In some examples, a graphic representation may comprise a design and controls editor. A design and controls editor comprises a means by which one or more users may input data including one or more of: design, patient numbers, randomization, and extension data. In some examples, a design and controls editor comprises multiple pages or panes where patient numbers and design inputs may be inputted separately.

In some examples, a graphic representation may comprise an interventions editor. An interventions editor comprises a means by which one or more users may input data corresponding to the name, dosage, frequency, formulation, and administrative route of drugs administered to patients during each period and segment of a trial.

Figure 11:
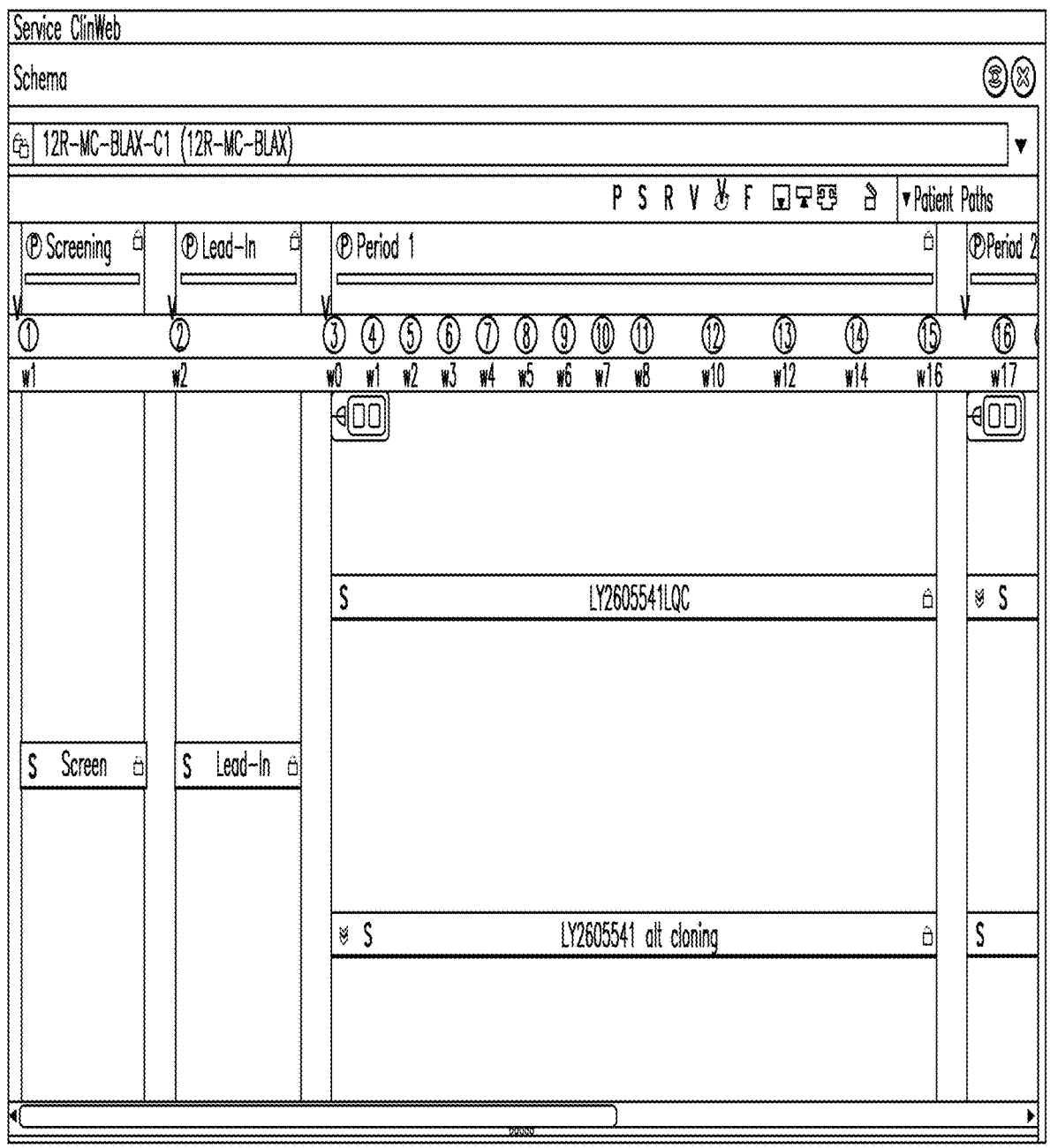
FIG. 11 is a diagram illustrating a schema editor according to one example.

FIG. 11 is a diagram illustrating a schema editor according to one example. In some examples, a schema editor comprises a means by which one or more users may add patient visits to a trial period and view data representing the structure of a trial candidate. For example, in the example illustrated in FIG. 11, the schema editor shows a screening period, a lead-in period, two treatment arms for period one, and two treatment arms for period two. In a clinical trial, a treatment arm represents the treatment(s) to be provided to the patient(s) participating in the trial. In some examples, the schema editor allows a user to input information into the schedule of events and view patient data and measures created with the efficacy and diagnostic indicators.

Figure 12:
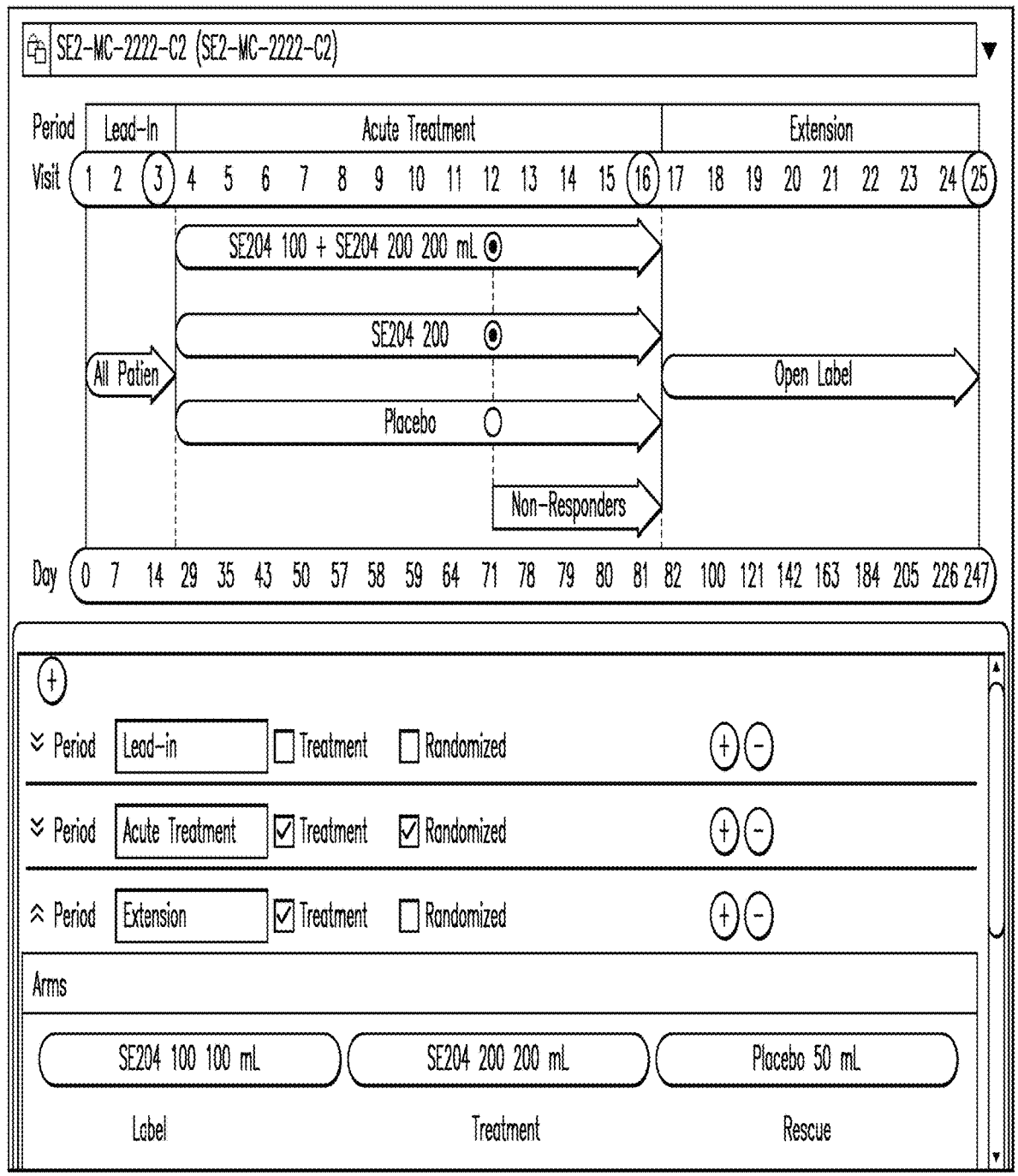
FIG. 12 is a diagram illustrating a schema editor according to another example.

FIG. 12 is a diagram illustrating a schema editor according to another example. In this example, the schema editor illustrates the assignment of drugs to treatment arms. Here, a user may utilize the schema editor to enter information regarding drug assignments in a particular treatment arm. In various examples, schema editors are provided in order to allow users to enter information regarding a variety of parameters.

Figure 13:
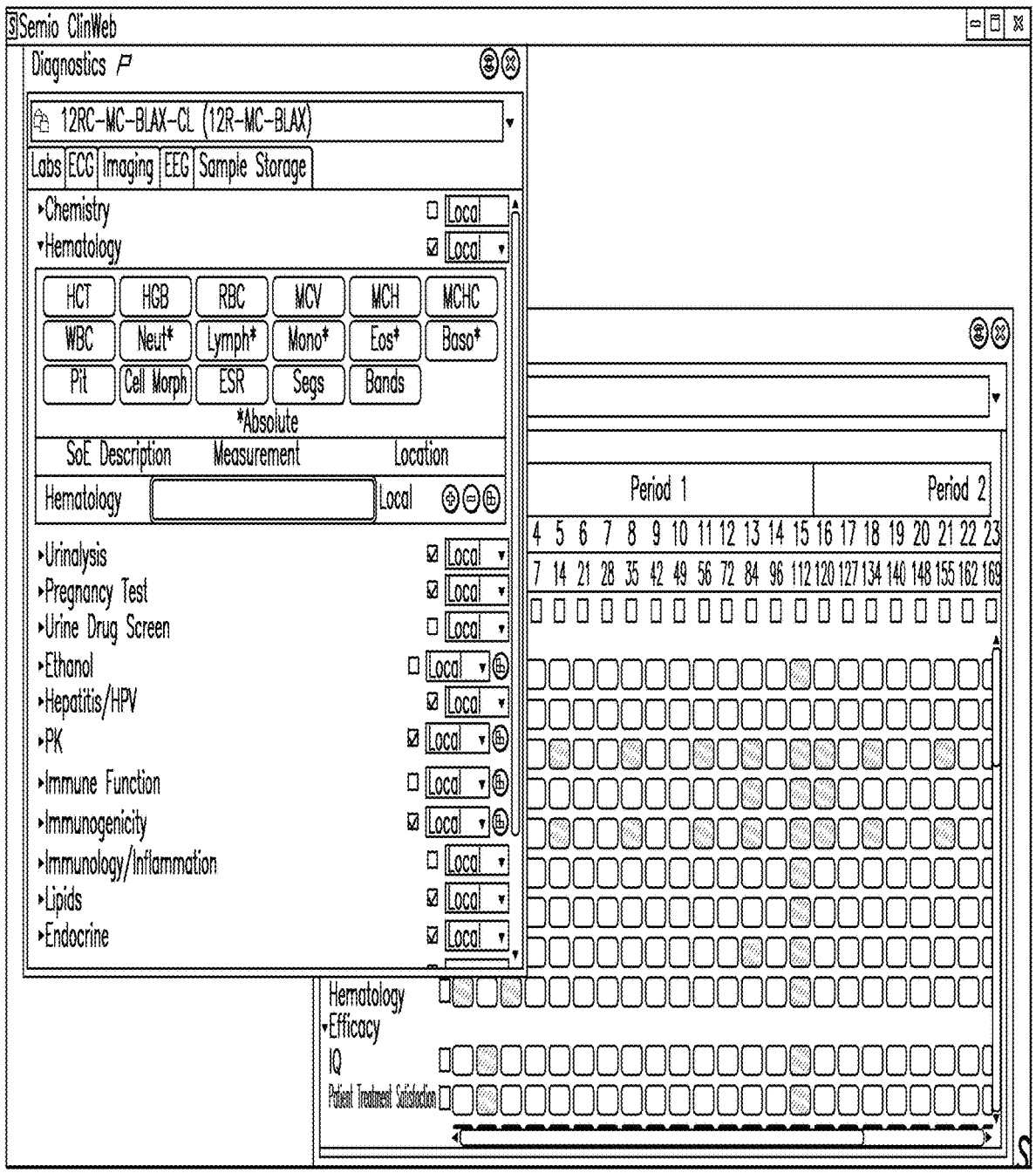
FIG. 13 is a diagram illustrating a schedule of events editor according to one example.

FIG. 13 is a diagram illustrating a schedule of events editor according to one example. In some examples, a schedule of events editor enables a user to designate what measures or corresponding samples will be obtained during which visits. In the example illustrated in FIG. 13, a schedule of events editor view shows weeks on a horizontal axis and measures on a vertical axis. A diagnostics editor view may also be launched from a schedule of events editor in some examples.

Also, in some examples, the schedule of events editor pulls patient visit data from the schema. The schedule of events editor may also pull measures from a list of measures. The list may be created with an efficacy editor and/or a diagnostic editor, such as those described herein. In some examples, when a user selects the intersection of a row and column, the user selects a measure corresponding to the selected row to be obtained during a visit corresponding to the selected column. The selection may also drive cost and patient burden associated with the measures to the particular visit. Accordingly, costs and burden can be forecasted on a regular (e.g., weekly, biweekly, monthly) basis. Such a schedule may be delivered to those needing such information such as study teams.

In some examples, a burden editor is provided. A burden editor comprises a means by which one or more users may input patient burden data, such as the time required of a patient to obtain input for a measure, and then receive a patient burden score representing an abstraction of the relative burden on a patient corresponding to a particular clinical plan. A method is disclosed in which measures corresponding to various demands, requirements, and burdens imposed on a patient by a particular clinical plan are mathematically combined into a single numeric abstraction. Next, the numeric abstraction is displayed to a user. The numeric abstraction is sometimes referred to as a burden score. In some examples, this numeric abstraction (or burden score) provides a means by which one or more users may observe and predict the likelihood that a patient will participate in a clinical trial.

When a burden score is high, this indicates a burdensome trial which will likely make it more difficult to recruit patients to participate in the trial. In some examples, the overall burden of a particular trial candidate is displayed in the trial candidate dashboard.

Figure 14:
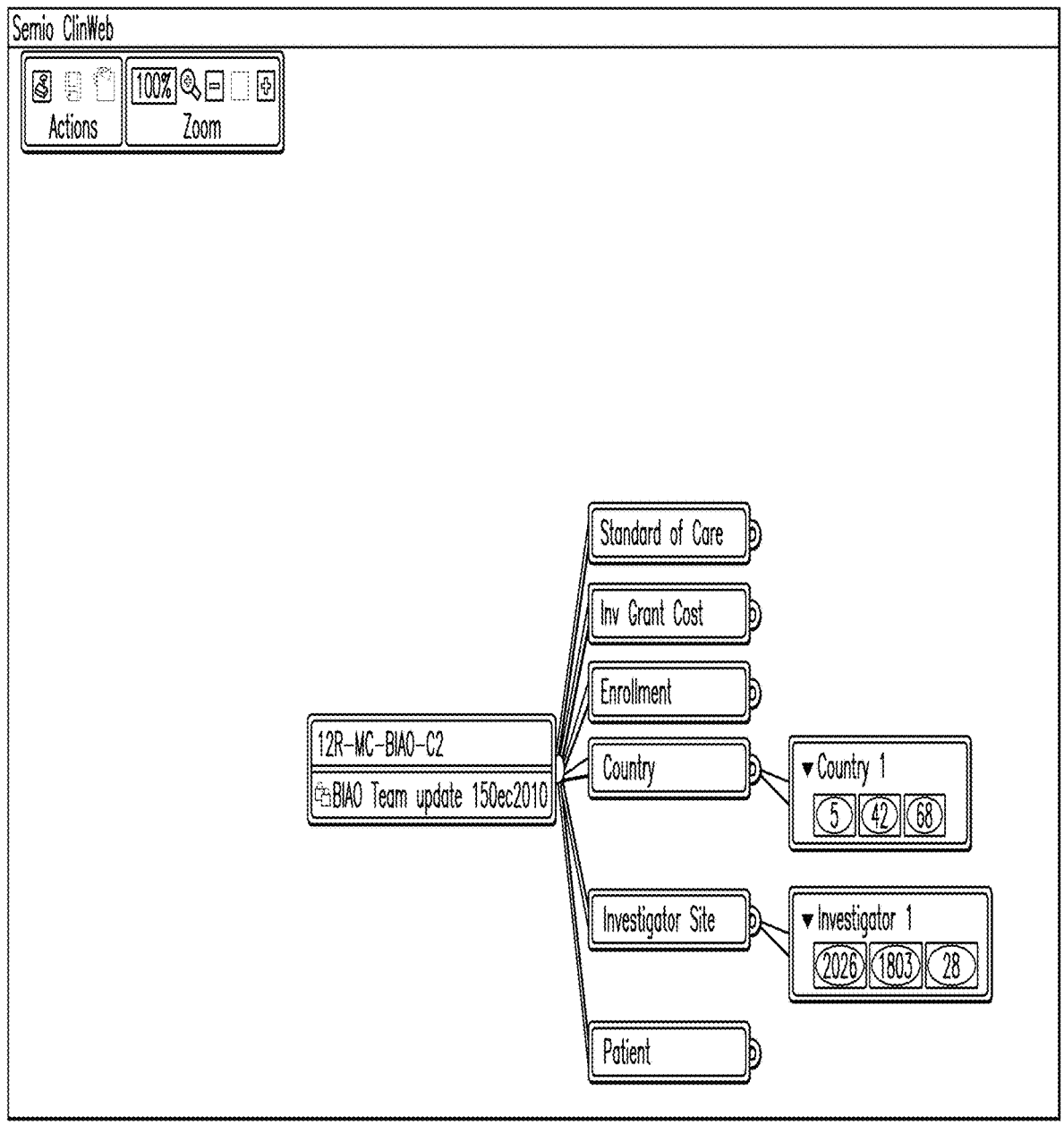
FIG. 14 is a diagram illustrating a predictive analytics dashboard according to one example.

FIG. 14 is a diagram illustrating a predictive analytics dashboard according to one example. In some examples, a predictive analytics dashboard comprises a means by which one or more users may instantiate one or more editors to enter and display enrollment or other data and combine said data with proprietary and/or outsourced data to predict the impact of user choices. In the example illustrated in FIG. 14, the predictive analytics dashboard shows color-coded parameters of country and investigator site plans named "Country 1" and "Investigator 1." The color coding indicates the relative attractiveness of the particular courses of action. In some examples, the country and investigator site editors store country and investigator site plans that are subsequently accessed by the enrollment editor.

Figure 15:
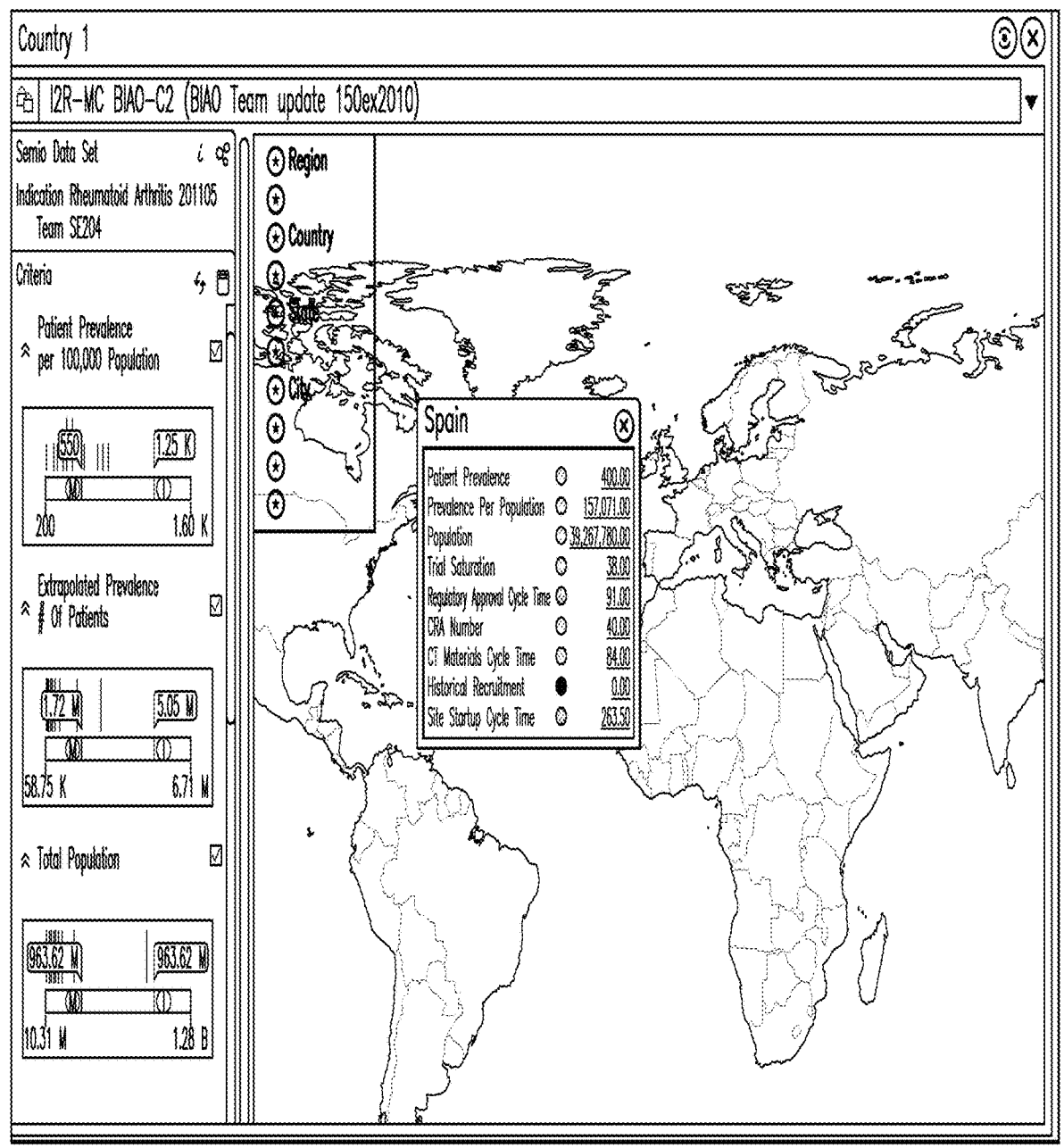
FIG. 15 is a diagram illustrating a country editor according to one example.

FIG. 15 is a diagram illustrating a country editor according to one example. In some examples, a country editor comprises a means by which one or more users may identify which countries have investigator sites likely to enroll the necessary patients for a clinical trial in a timely manner. This identification may be made based on proprietary historical information. In the example illustrated in FIG. 15, a country editor may comprise sliders for setting limits for data categories. In such examples, the sliders divide the data range into three sub-ranges. Data falling within the first sub-range is assigned the number 0; data falling in the middle sub-range is assigned the number 1; and data in the last sub-range is assigned the number 2. Categories may be colored according to their assigned values. For example, 0, 1, and 2 may correspond to the colors red, yellow, and green, respectively.

In some examples, the values for all of the categories for a particular country are averaged to determine the value for the country. For example, the country may be colored red if the value falls below 0.8; the country may be colored yellow if the value is between 0.8 and 1.2; and the country may be colored green if the value exceeds 1.2. Also, a country may be colored a different color (e.g., gray or white) to indicate the country cannot be selected for one reason or another.

Further, data in one or more categories may be compared to user-designated limits in each category. Examples of such categories include patient prevalence, extrapolated prevalence, total population, trial saturation, regulatory approval cycle time, clinical trial materials cycle time, historical recruitment, and site startup cycle time. Next, based on the comparison between the data and the user-designated data limits, a value and associated color-code are created representing an abstraction of how attractive a particular country is for inclusion in the clinical plan.

Figure 16:
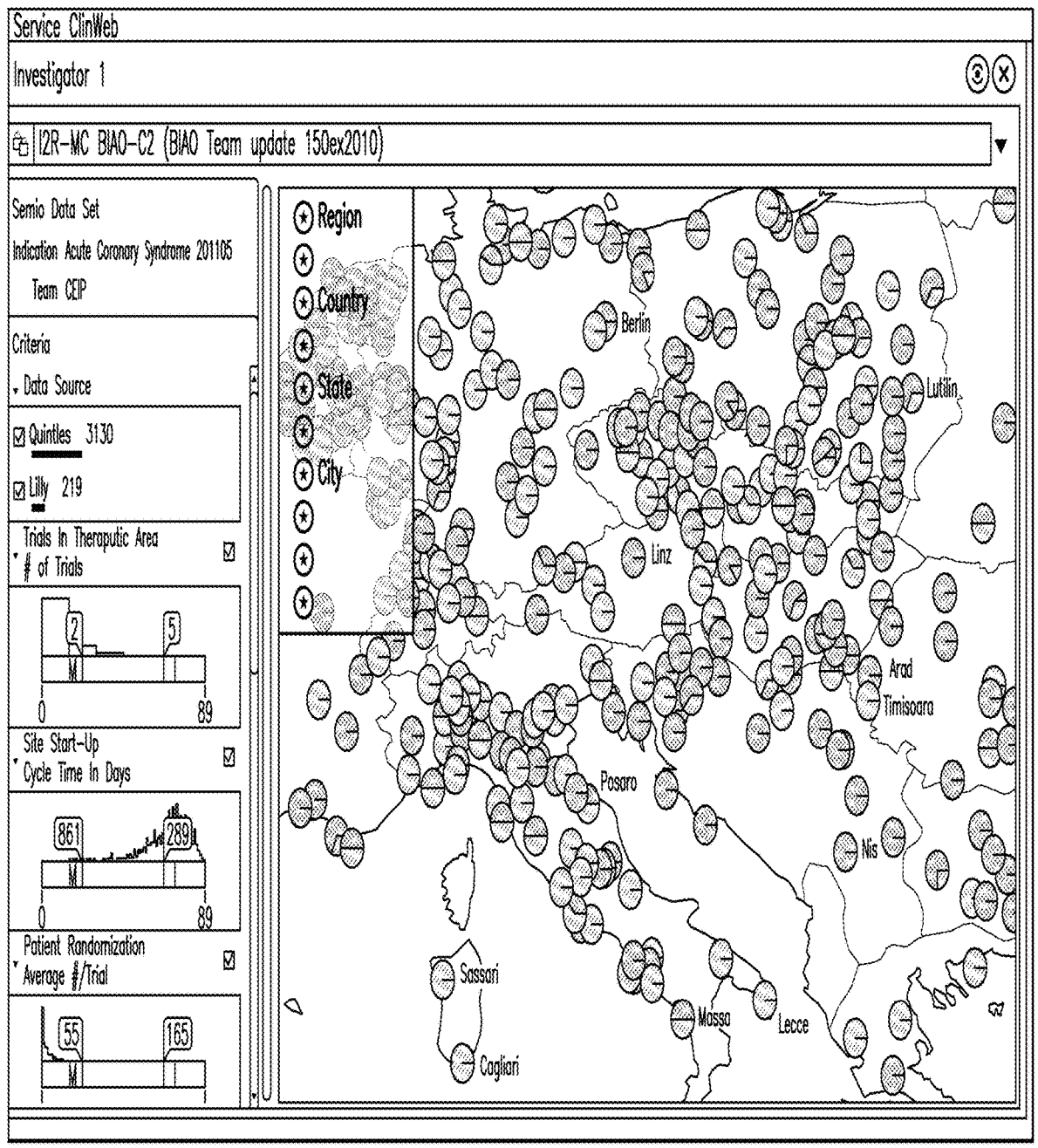
FIG. 16 is a diagram illustrating an investigator site editor according to one example.

FIG. 16 is a diagram illustrating an investigator site editor according to one example. In some examples, an investigator site editor comprises a means by which one or more users may view data representing the likelihood and timing of enrolling patients within geographical boundaries. In some examples, users can select geographical groupings such as countries, state, or cities for display. In some examples, data is represented to the user as color-coded circles representing the attractiveness of a particular investigator site. For example, the circles may be coded red, yellow, green, or some combination thereof.

FIGS. 17-22 are diagrams illustrating an enrollment editor according to various examples. In some examples, an enrollment editor allows a user to select an investigator site based on one or more criteria—for example, selected country and investigator site plans. According to one example, an enrollment editor comprises one or more panels and panes that comprise tables, graphs, lists, and other representations of data. For example, in the example illustrated in FIG. 17, an empty startup page is shown, signifying that no investigator site has been selected yet. A user may select one or more sites from the selection table by checking a selection button next to the desired site. As sites are added, the editor tallies various parameters, such as one or more of: the number of enrolled patients likely to be enrolled by the selected sites and/or site startup timing. For example, in the example illustrated in FIG. 18, a results panel is shown which includes a country summary showing sites that have been selected as well as the tallied parameters. In this example, 1113 patients are required and the results panel shows that 318 sites were selected in order to enroll 1114 patients.

In some examples, a user can select between various enrollment models. One such model is competitive enrollment in which sites are added according to the user's selections until the required number of patients is reached. Another model is allocated enrollment in which site selection is restricted by patient rules, which can be created by the enrollment editor. An example of a patient rule is a requirement that at least 50 patients must be in Germany and no more than 50 patients may be in Saudi Arabia. Another exemplary rule requires enrollment only of investigators capable of providing at least 100 patients.

Figure 19:
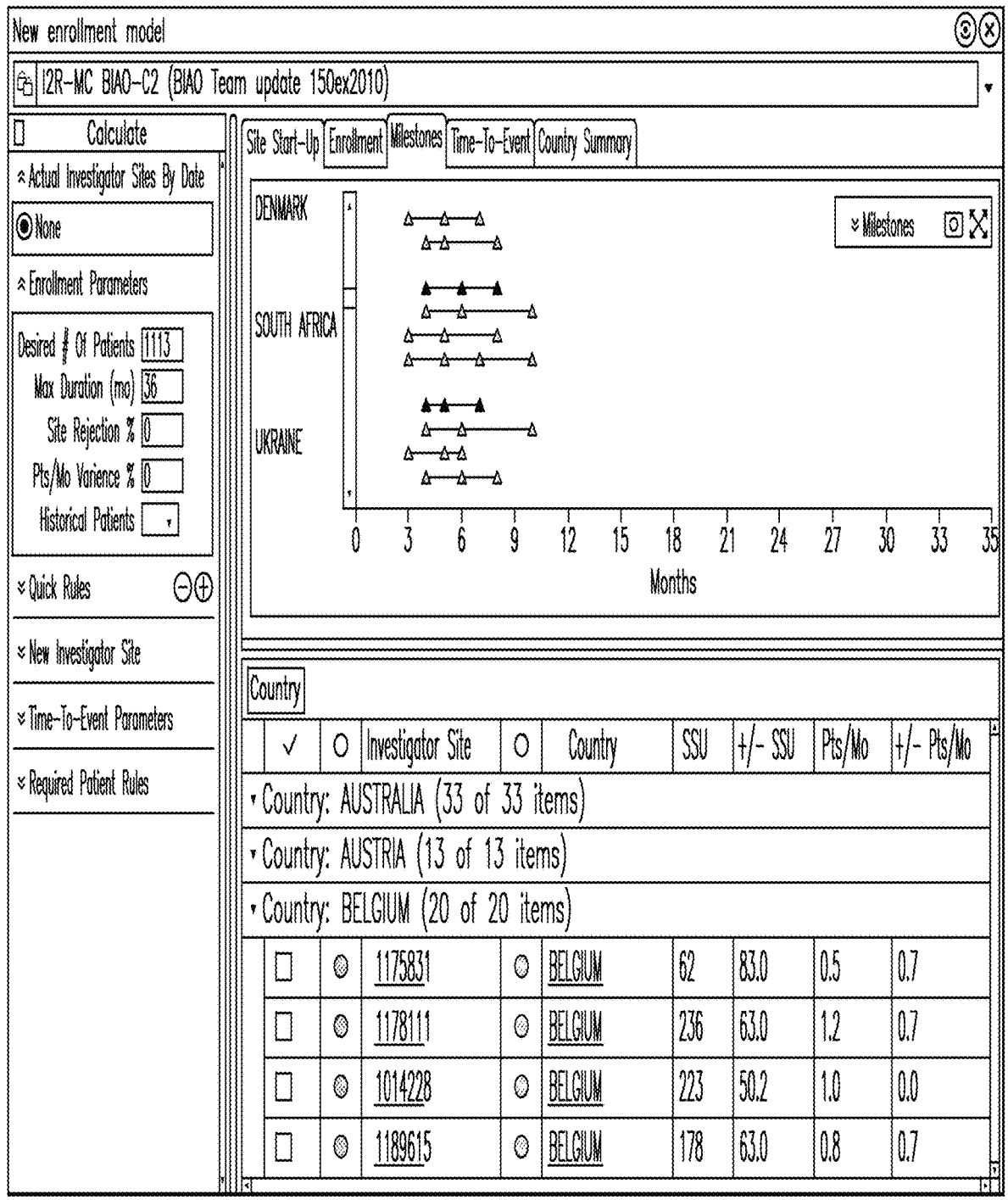
FIG. 19 is a diagram illustrating an enrollment editor according to one example.

In the example illustrated in FIG. 19, a graph is provided showing, in the results panel, the best, midline, and worst case first-patient visit milestones. In this example, the middle milestone represents the median of the sites in the country and the best/worst cases are computed by the median +/−a.

Figure 20:
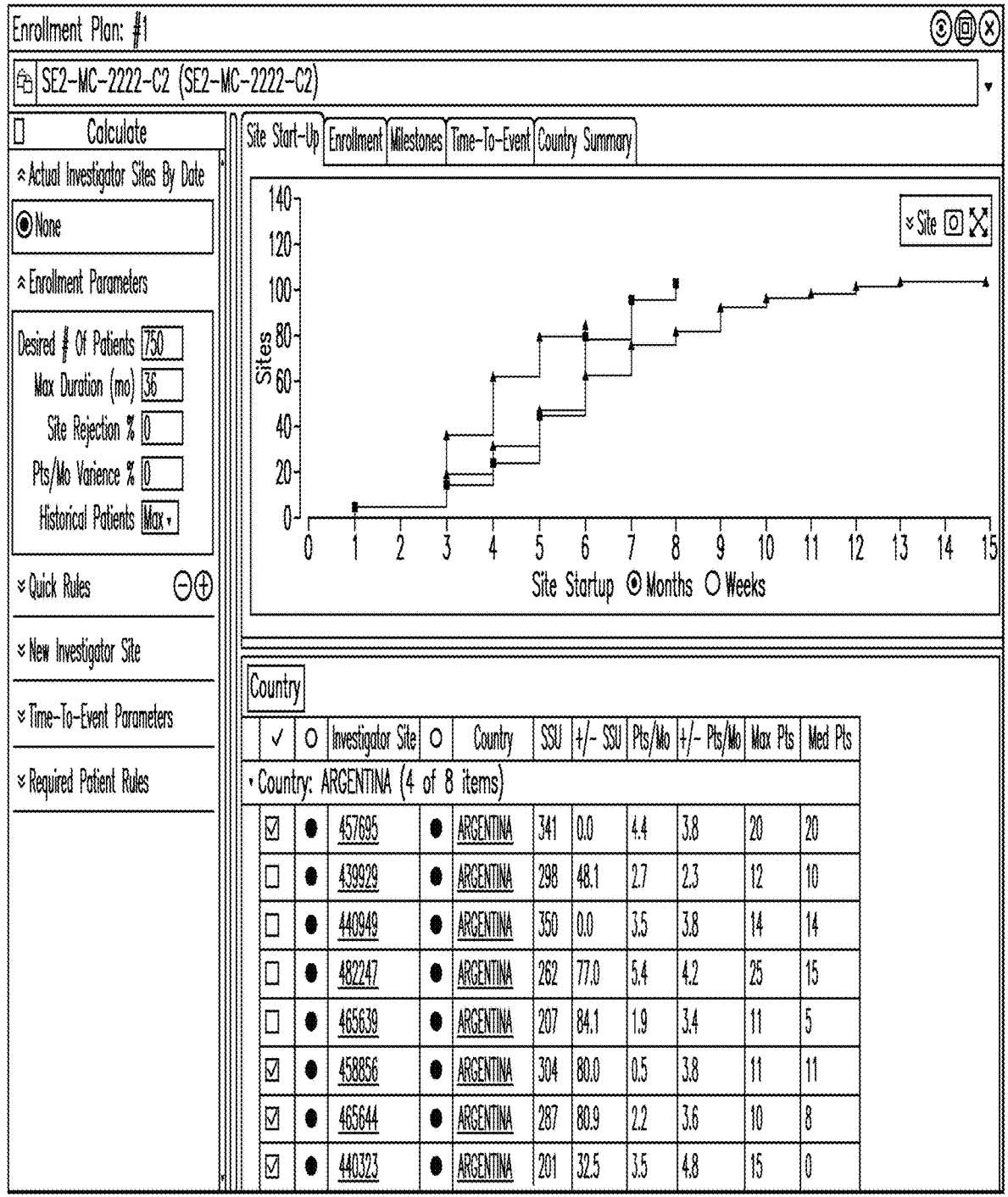
FIG. 20 is a diagram illustrating an enrollment editor according to one example.
Figure 21:
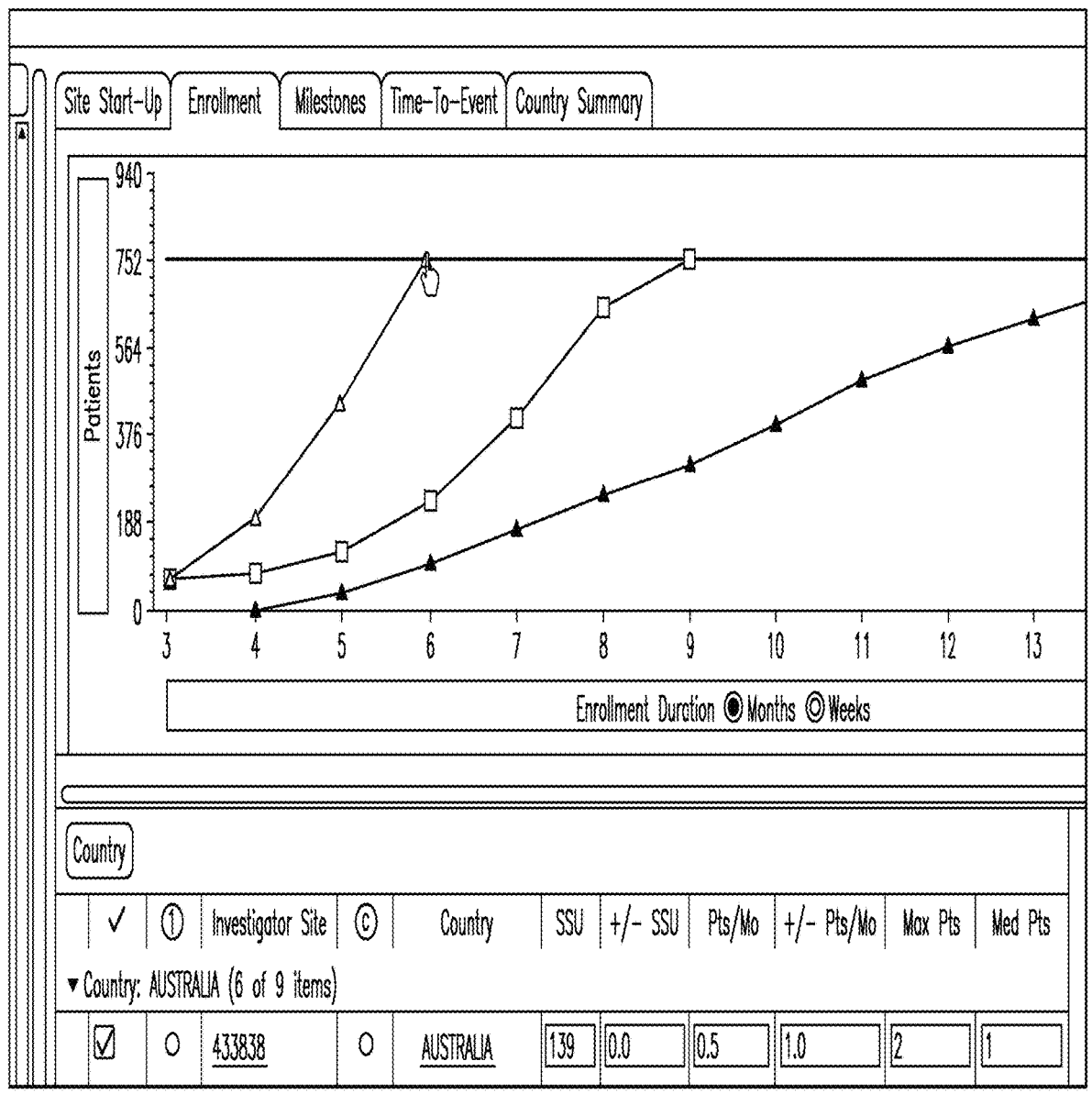
FIG. 21 is a diagram illustrating an enrollment editor according to one example.
Figure 22:
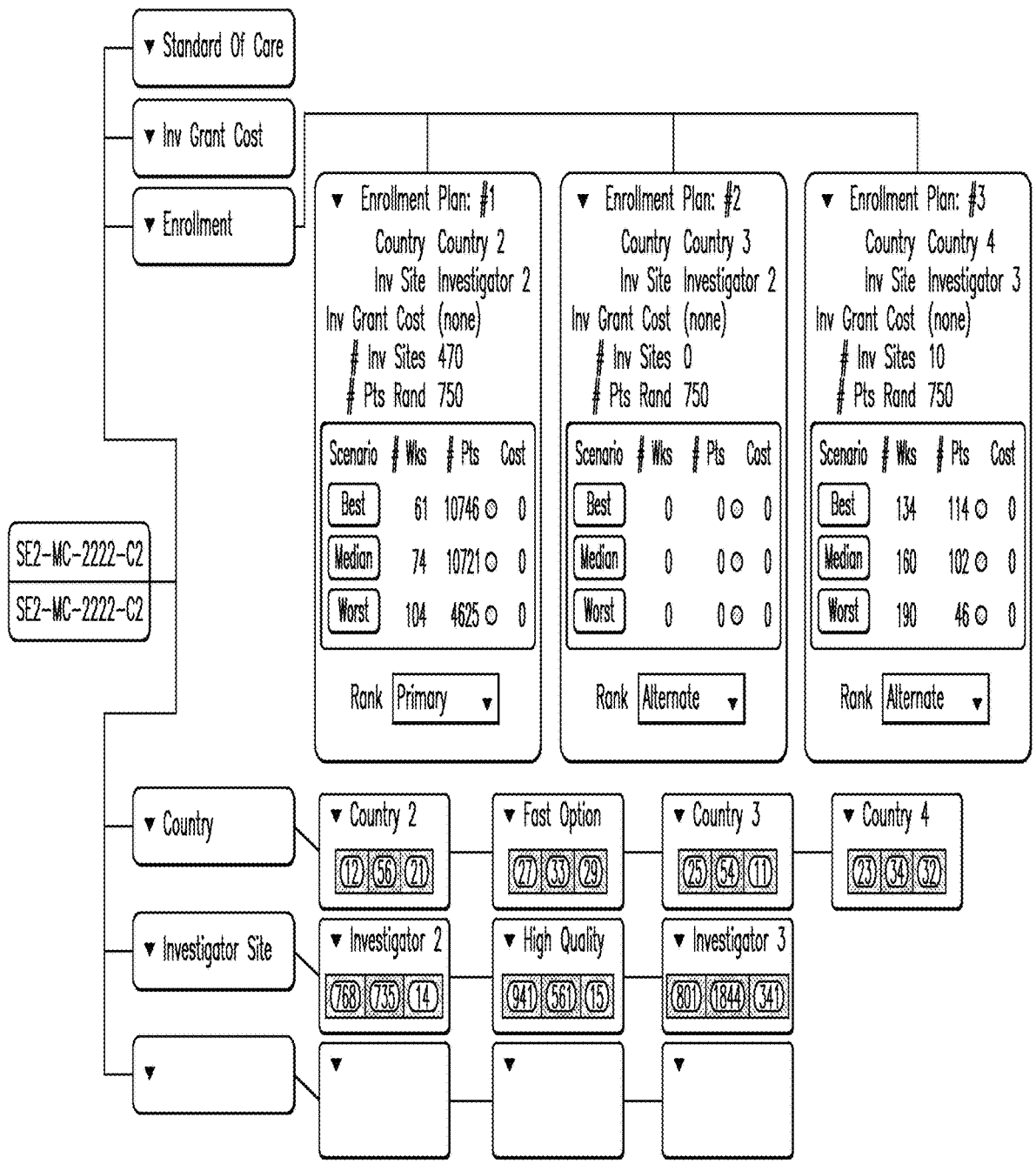
FIG. 22 is a diagram illustrating an enrollment editor according to one example.

In various examples, other graphs are provided. For example, FIG. 20 illustrates a graph showing how quickly sites start up as the number of sites increases. Also, FIG. 21 illustrates a graph showing enrollment duration as the number of patients increases.

In some examples, the enrollment editor enables users to develop multiple enrollment plans based on different country and investigator site plans. In the example illustrated in FIG. 22, enrollment plans are summarized on a predictive analytics dashboard. In the example illustrated in FIG. 22, three enrollment plans, four country plans, and three investigator site plans are depicted. For each enrollment plan (labeled "Enrollment Plan #1," "Enrollment Plan #2," and "Enrollment Plan #3"), the best, median, and worst case is shown. Also, for each country and investigator plan, the number of red, yellow, and green countries and investigator sites are shown.

In some examples, each enrollment plan is designated as primary, secondary, or alternate. There can only be one primary enrollment plan. The primary plan can be published by selecting the appropriate menu option from the primary plan node. In some examples, upon selection of the publication option, the user must also select a publication label. Examples of publication labels include forecast, re-forecast, baseline, or re-baseline.

Figure 23:
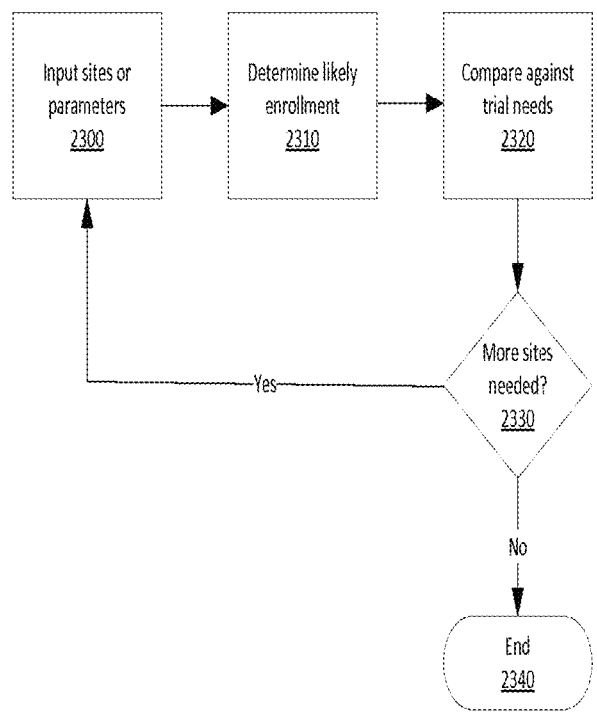
FIG. 23 is a flow chart illustrating site input according to one example.

FIG. 23 is a flow chart illustrating site input according to one example. In some examples, a user inputs one or more investigator sites and/or data parameters defining the enrollment needs for a clinical trial. Next, an algorithm determines the likely sum enrollment of all the selected investigator sites. Last, the sum enrollment is compared against the needs of a particular clinical trial to determine whether more or fewer investigator sites are needed to meet the parameters of the clinical trial.

Figure 24:
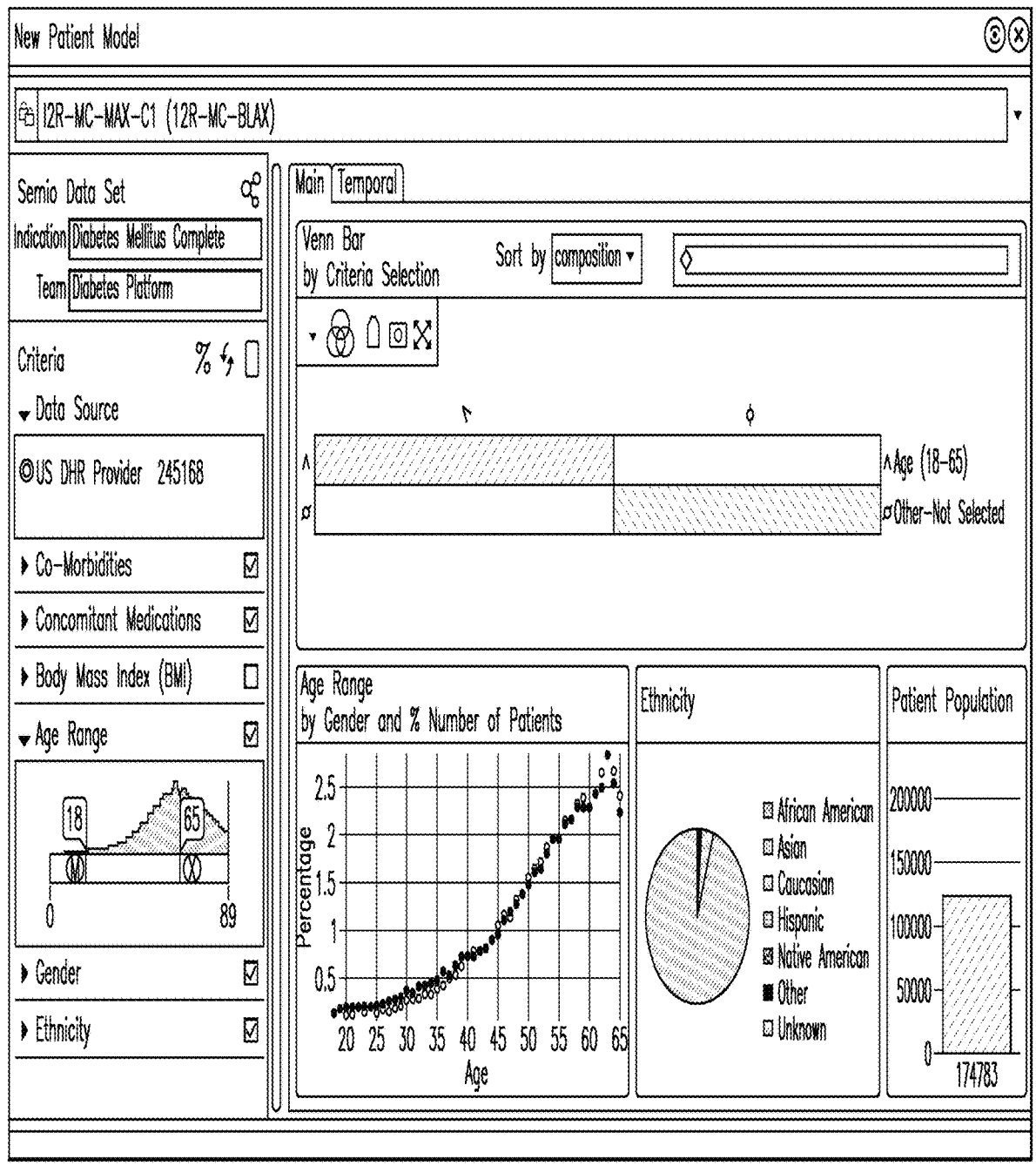
FIG. 24 is a diagram illustrating a patients editor according to one example.

FIG. 24 is a diagram illustrating a patients editor according to one example. In some examples, a patients editor comprises a means by which one or more users may enter information identifying optimal patient enrollment parameters. In some examples, such as the one illustrated in FIG. 24, a patients editor comprises sliders which users configure to set patient inclusion and exclusion limits within data categories. The data categories may include any relevant data, such as one or more of: co-morbidities, concomitant medications, body mass index, age, gender, and ethnicity. In some examples, a patients editor comprises graphs, tables, and other visual representations of data showing the number of patients included and excluded pursuant to user-defined criteria.

For example, in the example illustrated in FIG. 24, a Venn Bar diagram represents the exclusion and inclusion parameters and shows the number of included and excluded patients due to particular selection criteria. Users can manipulate the sliders to arrive at a desired number of potential patients. Further, the patient editor may present graphs, such as line and/or pie graphs of various facets, such as age and ethnicity. Further, a bar graph of the patient population based on selected facet limits may be provided.

Figure 25:
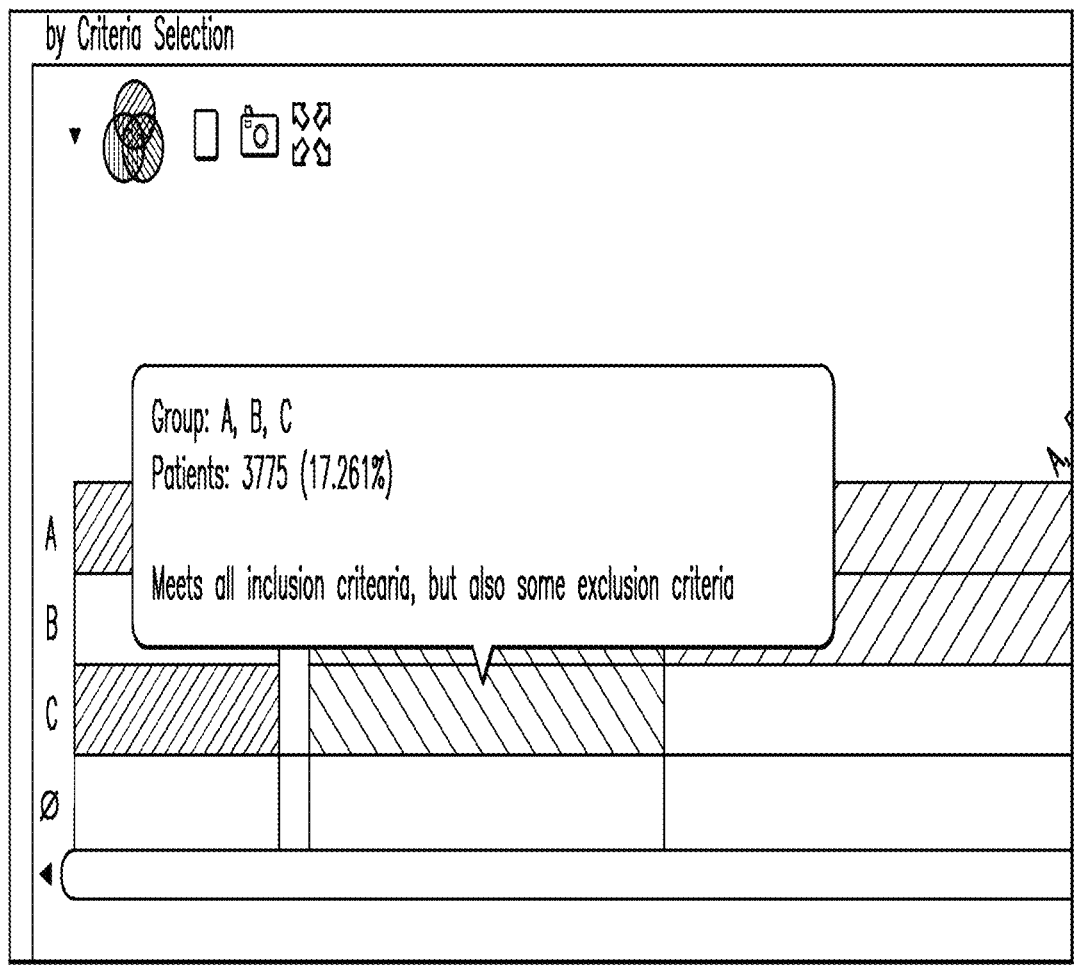
FIG. 25 is a diagram illustrating a patients editor according to one example.

FIG. 25 is a diagram illustrating a patients editor according to one example. Specifically, FIG. 25 depicts a portion of a Venn Bar diagram. In this illustrative example, Venn fragment A represents age criteria, fragment B represents a history of cardiovascular disease, and fragment C represents the absence of opioid agonists. In some examples, upon selection of a fragment a popup window displays the number of patients represented by the fragment.

In some examples, a standard of care editor is provided. A standard of care editor comprises a means by which one or more users may select comparator drugs for trials. In some examples, a standard of care editor comprises graphs, tables, and other visual representations of data showing exemplary standards of care for one or more patients.

Figure 26:
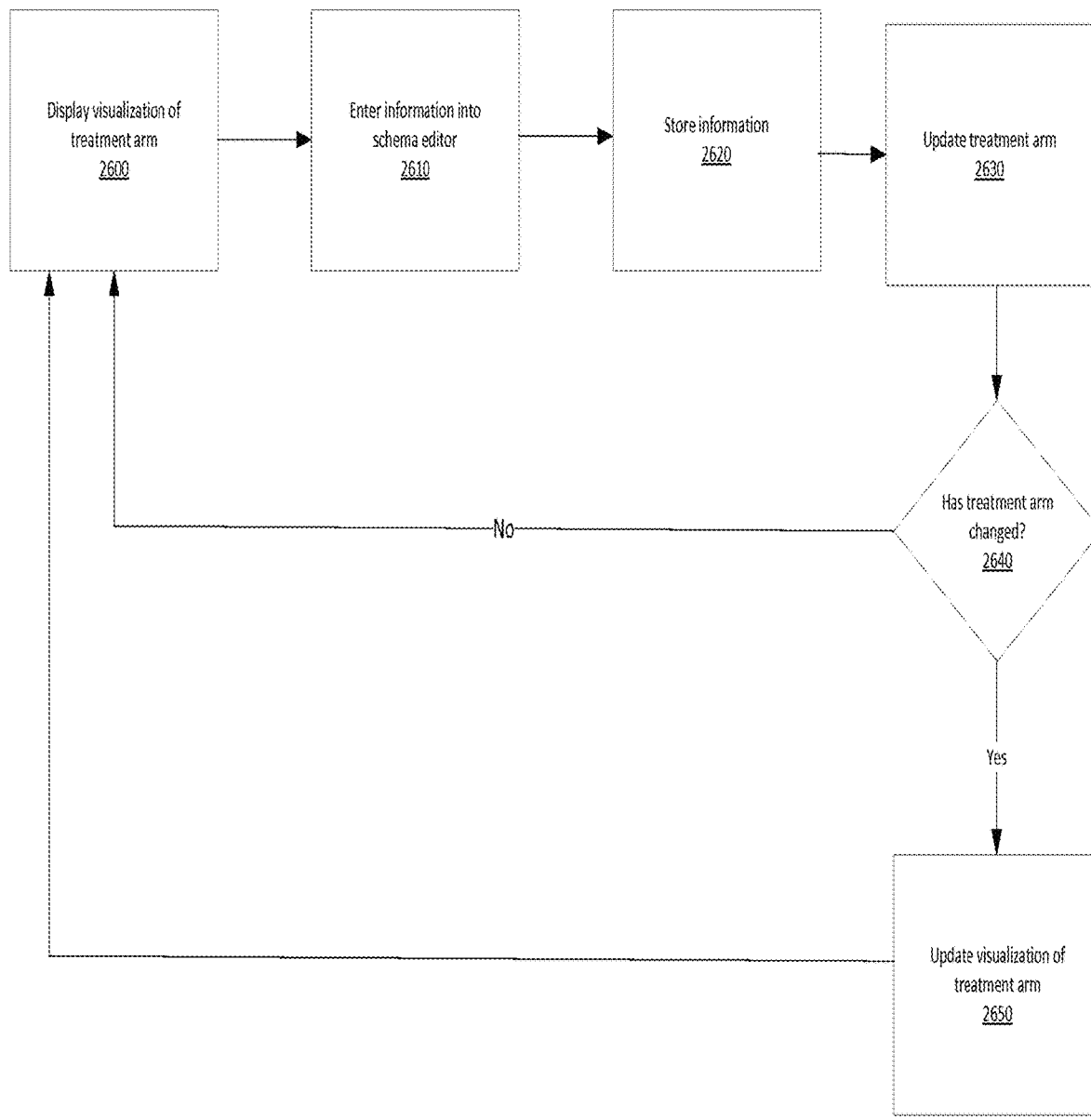
FIG. 26 is a flow chart illustrating use of a schema editor according to one example.

FIG. 26 is a flow chart illustrating use of a schema editor according to one example. As discussed herein, examples according to this disclosure provide a schema editor. A user may enter information into the schema editor via the client 100, and the schema editor may be executed as one or more processes on one or more of the client 100, Application Server 200, and web server 300. Further, in some examples the schema editor accesses and/or updates information stored in the database 400.

Turning to FIG. 26, some examples display a visualization of a treatment arm 2600. As discussed herein, a treatment arm represents the treatment(s) to be provided to the patient (s) participating in the trial. An example of a visualization of a treatment arm is shown in FIG. 12.

Next, according to some examples, a user may enter information into the schema editor 2610. The information may include any information relevant to the schema of a trial. For example, the schema editor may allow the user to enter information about the patient population and the treatments they will receive—e.g., drug treatment(s), biopsy, blood test(s), questionnaires, and the like.

According to some examples, the information entered into the schema editor is stored 2620. For example, the information may be stored in the database 400. This illustrates a benefit of some examples according to this disclosure. In prior art systems, information about trial schemas was stored in a variety of documents, such as spreadsheets, word processing documents, and the like. While efforts were often made to keep such documents in a common repository, such as a shared network drive, there was not a single database of trial information. Thus, if information contained in one document was relevant to the subject matter of another document, a user was required to manually copy that information from one document to the other. This led to needless duplication of effort and increased the likelihood of errors in transcription. However, as shown herein, examples according to this disclosure store the information in a centralized location that can be accessed by the relevant processes. An effect of this is that a particular piece of information need only be entered one time, and after that it is available to other processes that need the information.

Next, according to some examples, the treatment arm is updated based on the information entered 2630. For example, if a user entered a particular drug regimen into the schema editor, the corresponding treatment arm is updated to include that drug regimen. This updating is done dynamically.

Next, according to some examples, a determination is made whether the treatment arm has changed 2640. If the treatment arm has not changed, then the visualization remains the same. If the treatment arm has changed, then the visualization of the treatment arm is updated to include the change 2650.

Examples according to this disclosure may also include a schedule of events which provides information such as measurements, scales, and the like, based on the information entered into the schema editor. The schedule of events is dynamically generated from changes made to the schema. This illustrates a benefit of some examples according to this disclosure. In prior art systems, a user was required to make two changes—one to the schema and one to the schedule. However, examples according to this disclosure allow a user to make a change in one place (the schema editor) and the change is populated elsewhere (to the schedule of events). This has numerous benefits. For example, it saves duplicative labor. Also, it reduces the chance of error because under the prior art systems, a user could make a mistake while entering the information a second time.

Although many examples described in the present disclosure relate to clinical trial planning and design, it should be understood that the scope of the present disclosure is intended to encompass other applications where predictive clinical planning and design are used in research and development. Other advantages will become apparent to one of ordinary skill in the art from an understanding of the present disclosure.

The foregoing description of the examples according to this disclosure has been presented only for the purpose of illustration and description and is not intended to be exhaustive or to limit the invention to the precise forms disclosed. Numerous modifications and adaptations are apparent to those skilled in the art without departing from the spirit and scope of this disclosure.

That which is claimed is:

1. A method of planning and designing a clinical trial using visual representations on a computing device, the method comprising steps of:
    instantiating, on the computing device, a plurality of data objects, each comprising one or more data items pertaining to the clinical trial;
    establishing, on the computing device, a hierarchically connected plurality of graphical nodes by selecting, and forming a connection between, source and destination graphical nodes of the plurality of graphical nodes, each representing instantiated data objects of the plurality of data objects;
    graphically presenting, on the computing device, at least a portion of the clinical trial using the plurality of hierarchically connected graphical nodes each forming a preceding and/or one or more child graphical nodes, wherein the data objects represented by the preceding graphical nodes reference or are referenced by the data objects represented by the child graphical nodes, and the one or more data items are modifiable within the plurality of graphical nodes;
    propagating
    the one or more data items of the source graphical node to the destination graphical node via the plurality of hierarchically connected graphical nodes, and
    an association between the one or more data items of the source and destination graphical nodes based on a condition;
    selecting a first of the plurality of graphical nodes;
    modifying at least one of the one or more data items of the respective data object of the selected first graphical node;
    propagating the modification to the one or more data items of the preceding and child graphical nodes of the first graphical node, the propagation modifying a corresponding data item of the respective preceding and child graphical nodes; and
    expanding the graphical presentation, within the at least one of the first, preceding and child graphical nodes, by displaying the modified one or more data items.

2. The method of claim 1, wherein each of the child graphical nodes is hierarchically connected to include preceding and child graphical nodes.

3. The method of claim 1, further comprising steps of:
    selecting one of the one or more data items associated with a data object of a second graphical node;
    establishing a relationship between the data items associated with the first and second graphical nodes; and
    propagating a data value associated with the data item of the first graphical node to the data item of the second graphical node.

4. The method of claim 1, wherein the clinical trial comprises one or more sites, and the clinical trial information comprises one or more data items each describing one of patient information associated with one or more patients for the clinical trial, investigator information associated with one or more investigators for the clinical trial, and enrollment information associated with enrollment criteria for the clinical trial, and further comprising steps of:
    associating the one or more data items describing the patient information, the investigator information, and the enrollment information to develop a map of sites for the clinical trial; and
    determining at least one potential site of the one or more sites for the clinical trial from the map of sites based at least in part on the associations.

5. The method of claim 4, further comprising a step of: determining patient enrollment totals at the one or more potential sites based at least in part on at least one of the patient information, the investigator information, the enrollment information, and the associations, wherein each of the patient enrollment totals corresponds to a prediction for a total number of patients enrolled in the clinical trial.

6. The method of claim 5, further comprising a step of: graphically presenting the patient enrollment totals at the one or more potential sites, the graphical representation corresponding to alternative scenarios for enrollment in the clinical trial.

7. The method of claim 4, further comprising steps of:
determining, using at least one of the patient enrollment totals, whether more or fewer than the one or more sites are needed for the clinical trial;
adding sites to the one or more sites determined needed for the clinical trial;
and removing sites from the one or more sites determined not needed for the clinical trial.

8. The method of claim 4, further comprising step of: generating a historical metric by comparing one or more previous clinical trials to at least a portion of one of the patient information, investigator information, or the enrollment information, wherein determining at least one of the patient enrollment totals is further based in part on the historical metric.

9. A non-transitory computer-readable medium comprising processor-executable program code configured to cause a processor to perform a method of planning and designing a clinical trial using visual representations on a computing device, the method comprising steps of:
instantiating, on the computing device, a plurality of data objects, each comprising one or more data items pertaining to the clinical trial;
establishing, on the computing device, a hierarchically connected plurality of graphical nodes by selecting, and forming a connection between, source and destination graphical nodes of the plurality of graphical nodes, each representing instantiated data objects of the plurality of data objects;
graphically presenting, on the computing device, at least a portion of the clinical trial using the plurality of hierarchically connected graphical nodes each forming a preceding and/or one or more child graphical nodes, wherein the data objects represented by the preceding graphical nodes reference or are referenced by the data objects represented by the child graphical nodes, and the one or more data items are modifiable within the plurality of graphical nodes;
propagating
the one or more data items of the source graphical node to the destination graphical node via the plurality of hierarchically connected graphical nodes, and
an association between the one or more data items of the source and destination graphical nodes based on a condition;
selecting a first of the plurality of graphical nodes;
modifying at least one of the one or more data items of the respective data object of the selected first graphical node;
propagating the modification to the one or more data items of the preceding and child graphical nodes of the first graphical node, the propagation modifying a corresponding data item of the respective preceding and child graphical nodes; and
expanding the graphical presentation, within the at least one of the first, preceding, and child graphical nodes by displaying the one or more modified data items.

10. The non-transitory computer-readable medium of claim 9, wherein: each of the child graphical nodes is hierarchically connected to include preceding and child graphical nodes.

11. The non-transitory computer-readable medium of claim 9, further comprising steps of:

selecting one of the one or more data items associated with a data object of a second graphical node;
establishing a relationship between the data items associated with the first and second graphical nodes; and
propagating a data value associated with the data item of the first graphical node to the data item of the second graphical node.

12. The non-transitory computer-readable medium of claim 9, wherein the clinical trial comprises one or more sites, and the clinical trial information comprises one or more data items each describing one of patient information associated with one or more patients for the clinical trial, investigator information associated with one or more investigators for the clinical trial, and enrollment information associated with enrollment criteria for the clinical trial, and further comprising steps of:
associating the one or more data items describing the patient information, the investigator information, and the enrollment information to develop a map of sites for the clinical trial; and
determining at least one potential site of the one or more sites for the clinical trial from the map of sites based at least in part on the associations.

13. The non-transitory computer-readable medium of claim 12, further comprising a step of: determine determining patient enrollment totals at the one or more potential sites based at least in part on at least one of the patient information, the investigator information, the enrollment information, and the associations, wherein each of the patient enrollment totals corresponds to a prediction for a total number of patients enrolled in the clinical trial.

14. The non-transitory computer-readable medium of claim 13, further comprising a step of: graphically presenting the patient enrollment totals at the one or more potential sites, the graphical representation corresponding to alternative scenarios for enrollment in the clinical trial.

15. The non-transitory computer-readable medium of claim 12, further comprising step of: generating a historical metric by comparing one or more previous clinical trials to at least a portion of one of the patient information, investigator information, or the enrollment information, wherein determining at least one of the patient enrollment totals is further based in part on the historical metric.

16. The non-transitory computer-readable medium of claim 12, further comprising steps of:
determining, using at least one of the patient enrollment totals, whether more or fewer than the one or more sites are needed for the clinical trial;
adding sites to the one or more sites determined needed for the clinical trial;
and removing sites from the one or more sites determined not needed for the clinical trial.

17. A system for planning and designing a clinical trial using visual representations on a computing device, the system comprising:
a processor is to:
instantiate a plurality of data objects, each comprising one or more data items pertaining to the clinical trial;
establish a hierarchically connected plurality of graphical nodes by selecting, and forming a connection between, source and destination graphical nodes of the plurality of graphical nodes, each representing instantiated data objects of the plurality of data objects;
graphically present at least a portion of the clinical trial using the as a plurality of hierarchically connected graphical nodes each forming a preceding and/or one or more child graphical nodes, wherein the data objects represented by the preceding graphical nodes reference or are referenced by the data objects represented by the child graphical nodes, and the one or more data items are modifiable within the plurality of graphical nodes;

propagate the one or more data items of the source graphical node to the destination graphical node via the plurality of hierarchically connected graphical nodes, and an association between the one or more data items of the source and destination graphical nodes based on a condition;

select a first of the plurality of graphical nodes;

modify at least one of the one or more data items of the respective data object of the selected first graphical node;

propagate the modification to the one or more data items of the preceding and child graphical nodes of the first graphical node, the propagation modifying a corresponding data item of the respective preceding and child graphical nodes; and expand the graphical presentation within the at least one of the first preceding, and child graphical nodes, by displaying the modified one or more data items.

18. The system of claim 17, wherein each of the child graphical nodes are hierarchically connected to include preceding and child graphical nodes.

19. The system of claim 18, wherein the processor is to:

select one of the one or more data items associated with a data object of a second graphical node;

establish a relationship between the data items associated with the first and second graphical nodes; and propagate a data value associated with the data item of the first graphical node to the data item of the second graphical node.

\* \* \* \* \*